(12) United States Patent
Zhang

(10) Patent No.: US 10,287,296 B2
(45) Date of Patent: May 14, 2019

(54) PROCESS FOR THE PREPARATION OF (S)-2-((4R,4AS,6R,7R,7AR,12BS)-7,9-DIMETHOXY-1,2,3,4,5,6,7,7A-OCTAHYDRO-4A,7-ETHANO-4,12-METHANOBENZO-FURO[3,2-E]ISOQUINOLIN-6-YL)-3,3-DIMETHYLBUTAN-2-OL

(71) Applicant: Noramco, Inc., Athens, GA (US)

(72) Inventor: Wen-Chun Zhang, Bogart, GA (US)

(73) Assignee: Noramco, Inc., Wilmington, DE (US)

(*) Notice: Subject to any disclaimer, the term of this patent is extended or adjusted under 35 U.S.C. 154(b) by 0 days.

(21) Appl. No.: 15/291,402

(22) Filed: Oct. 12, 2016

(65) Prior Publication Data

US 2017/0101415 A1 Apr. 13, 2017

Related U.S. Application Data

(60) Provisional application No. 62/240,329, filed on Oct. 12, 2015.

(51) Int. Cl.
*C07D 489/12* (2006.01)

(52) U.S. Cl.
CPC .................. *C07D 489/12* (2013.01)

(58) Field of Classification Search
CPC ........................ C07D 489/12; C07D 489/02
USPC ...................................... 546/39, 44
See application file for complete search history.

(56) References Cited

U.S. PATENT DOCUMENTS

| | | | | |
|---|---|---|---|---|
| 8,546,572 | B2 * | 10/2013 | Patel | C07D 489/10 546/44 |
| 9,701,687 | B2 * | 7/2017 | Cardot | C07D 489/12 |
| 2006/0100435 | A1 | 5/2006 | Sun et al. | |
| 2008/0125592 | A1 | 5/2008 | Huang et al. | |
| 2011/0313163 | A1 | 12/2011 | Hudlicky et al. | |
| 2014/0364612 | A1 | 12/2014 | Saxena et al. | |

FOREIGN PATENT DOCUMENTS

| | | |
|---|---|---|
| DE | 1173104 B | 7/1964 |
| WO | WO-2009/122436 A2 | 10/2009 |
| WO | WO-2013/050748 A2 | 4/2013 |

OTHER PUBLICATIONS

PCT International Search Report and Written Opinion of the International Searching Authority for application PCT/US2016/056540 dated Jan. 9, 2017, 9 pages.
Hudlicky et al. "Recent Advances in Process Development for Opiate-Derived Pharmaceutical Agents", Canadian Journal of Chemistry, Jan. 9, 2015, vol. 93, pp. 492-501.
Extended European Search Report for Application 16856069.6 dated Feb. 18, 2017, 8 pages.
Bentley et al. "Novel Analgesic and Molecular Rearrangement in the Morphine-Thebaine Group II, Alcohols Derived from 6,14-endo-Etheno-and 6,14-endo-Ethanotetrahydrothebaine" Journal of the America Chemical Society, Jun. 21, 1967, pp. 3273-3280.

\* cited by examiner

*Primary Examiner* — Charanjit Aulakh
(74) *Attorney, Agent, or Firm* — Alston & Bird LLP

(57) ABSTRACT

An invention includes a process for the preparation of (S)-2((4R,4aS,6R,7R,7aR,12bS)-7,9-dimethoxy-1,2,3,4,5,6,7,7a-octahydro-4a,7-ethano-4,12-methanobenzofuro[3,2-e]isoquinolin-6-yl)-3,3-dimethylbutan-2-ol.

19 Claims, No Drawings

PROCESS FOR THE PREPARATION OF (S)-2-((4R,4AS,6R,7R,7AR,12BS)-7,9-DIMETHOXY-1,2,3,4,5,6,7,7A-OCTAHYDRO-4A,7-ETHANO-4,12-METHANOBENZO-FURO[3,2-E]ISOQUINOLIN-6-YL)-3,3-DIMETHYLBUTAN-2-OL

RELATED APPLICATIONS

This application claims the benefit of priority of U.S. Provisional Application No. 62/240,329, filed on Oct. 12, 2015, the entire content of which is incorporated herein by reference.

FIELD OF THE INVENTION

The invention is directed to a process for the preparation of (S)-2-((4R,4aS,6R,7R,7aR,12bS)-7,9-dimethoxy-1,2,3,4,5,6,7,7a-octahydro-4a,7-ethano-4,12-methanobenzofuro[3,2-e]isoquinolin-6-yl)-3,3-dimethylbutan-2-ol, which is a compound that is useful in the synthesis of buprenorphine.

BACKGROUND OF THE INVENTION

Buprenorphine is a semi-synthetic opioid derivative of thebaine that is used to treat opioid addiction in higher dosages (>2 mg), to control moderate acute pain in non-opioid-tolerant individuals in lower dosages (~200 μg), and to control moderate chronic pain in dosages ranging from 20-70 μg/hour.

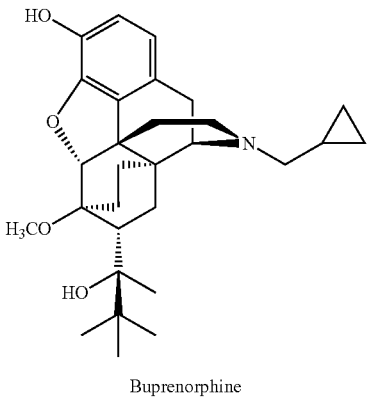

Buprenorphine

Buprenorphine is available in a variety of formulations: SUBUTEX, SUBOXONE, ZUBSOLV (buprenorphine HCl and naloxine HCl; typically used for opioid addition), TEMGESIC (sublingual tablets for moderate to severe pain), BUPRENEX (solutions for injection often used for acute pain in primary-care settings), NORSPAN, and BUTRANS (transdermal preparations used for chronic pain).

As an opioid, buprenorphine lends itself to some uses for which it has not been approved by the drug regulatory agency of the country in which it is used (such as the U.S. FDA). One such off-label use (perhaps the most common) is the use of SUBUTEX or SUBOXONE, a formulation intended solely for the treatment of opioid abuse, in palliation of severe pain with no neuralgic component or when the neuralgia is otherwise treated, such as with pregabalin. Niche pain indications, for which SUBUTEX or SUBOXONE may be a medication of choice, include obstruction of the small bowel; continuous nasogastric suction; oesophageal fistula; malignancy in the head or neck; and other cases where the patient is unable to swallow or this is difficult. Additionally, SUBUTEX or SUBOXONE may be an interesting alternative to sustained-release opioids such as morphine (MS CONTIN) and oxycodone (TARGIN).

Furthermore, buprenorphine is somewhat sleep-inducing, and may be of particular help when pain leads to sleeplessness. Other prototypical opioid side-effects may prove beneficial in the management of chronic pain, such as its characteristic euphoria (to alleviate depression due to pain, or in cases where the patient cannot tolerate or is resistant to conventional thymoleptic antidepressants), as well as its anxiolytic effects. These effects manifest themselves chiefly when buprenorphine is used in patients not tolerant to opioids; use of a partial agonist such as buprenorphine in those tolerant or dependent will simply lead to precipitated withdrawal (if a different opioid is used concomitantly) or relief of withdrawal (if used as monotherapy).

There remains a need for process(es) for the preparation of intermediates in the synthesis of buprenorphine, which process(es) are suitably for large scale/commercial manufacture, preferably process(es) which require fewer steps and/or fewer distillations and/or fewer isolation steps than current processes, while maintaining or improving overall product yield and/or purity.

SUMMARY OF THE INVENTION

In an embodiment, the invention is directed to a 2-pot, 5-reaction step process for the preparation of (S)-2-((4R,4aS,6R,7R,7aR,12bS)-7,9-dimethoxy-1,2,3,4,5,6,7,7a-octahydro-4a,7-ethano-4,12-methanobenzofuro[3,2-e]isoquinolin-6-yl)-3,3-dimethylbutan-2-ol, which is a compound useful in the synthesis of buprenorphine. More particularly, in the process of the invention, five reaction steps are telescoped such that only one intermediate may be isolated.

In an embodiment, the invention may include a process for preparing a compound of formula (I):

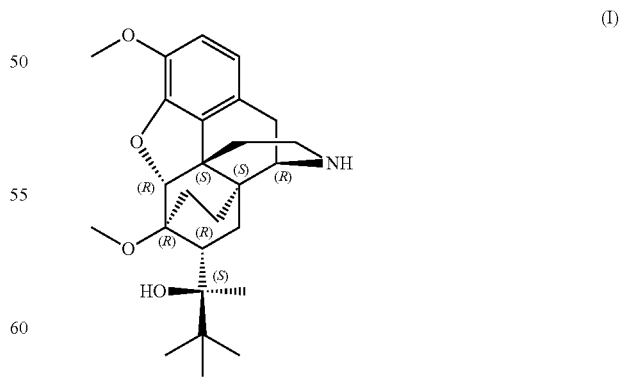

or a pharmaceutically acceptable salt thereof, comprising the steps of:

reacting a compound of formula (II) with methyl vinyl ketone as illustrated by the following schematic:

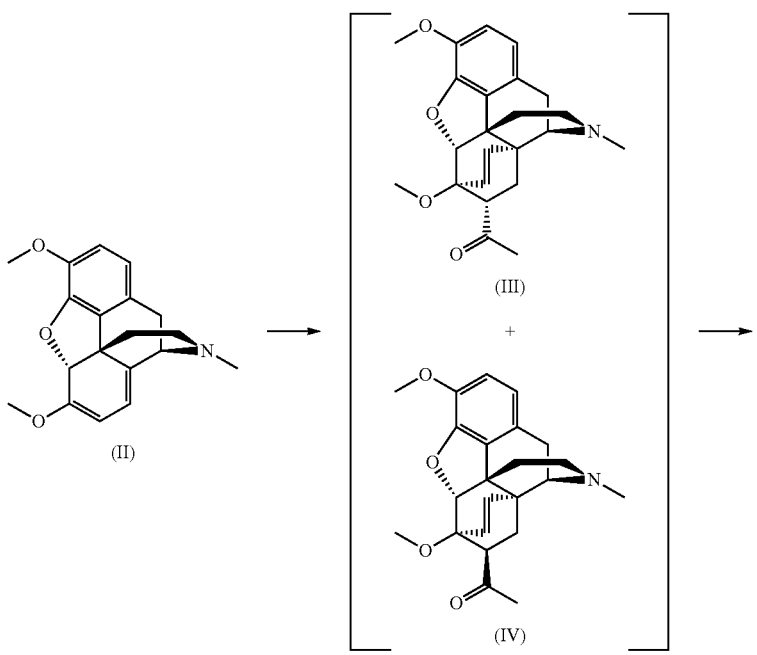

wherein the compound of formula (II) may be combined with the methyl vinyl ketone in a solution that may include an organic solvent, a mixture of organic solvents, or a mixture of water and an organic solvent, to provide a mixture of the compound of formula (III) and the compound of formula (IV), and wherein the reacting step may optionally include the step of isolating the compound of formula (III) or the compound of formula (IV);

azeotropically removing water and/or alcoholic solvent present in the mixture of the compound of formula (III) and the compound of formula (IV) to provide an anhydrous mixture of the compound of formula (III) and the compound of formula (IV);

reacting the anhydrous mixture of the compound of formula (III) and the compound of formula (IV) with a Grignard reagent as illustrated by the following schematic:

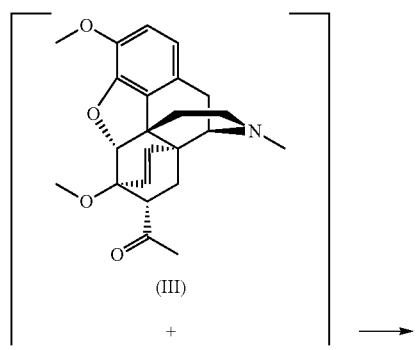

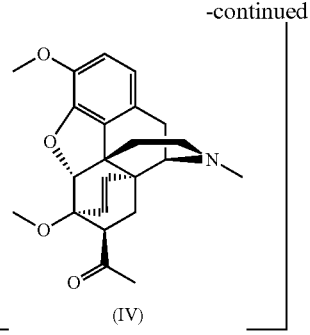

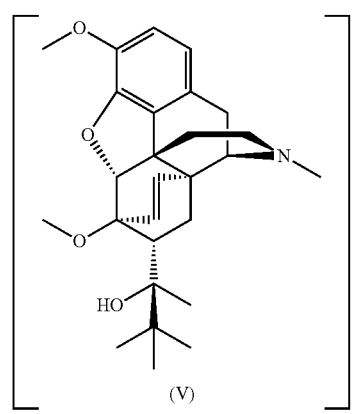

wherein the Grignard reagent may be selected from the group consisting of t-butyl MgCl, t-butyl MgBr, and t-butyl MgI, to provide a mixture that includes a compound of formula (V), and wherein the reacting step may optionally include the step of isolating the compound of formula (V);

hydrogenating the compound of formula (V) as illustrated by the following schematic:

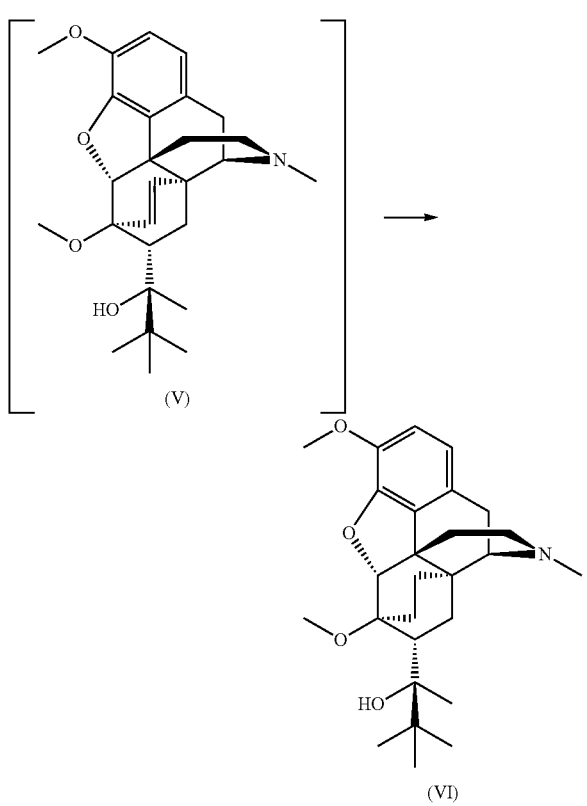

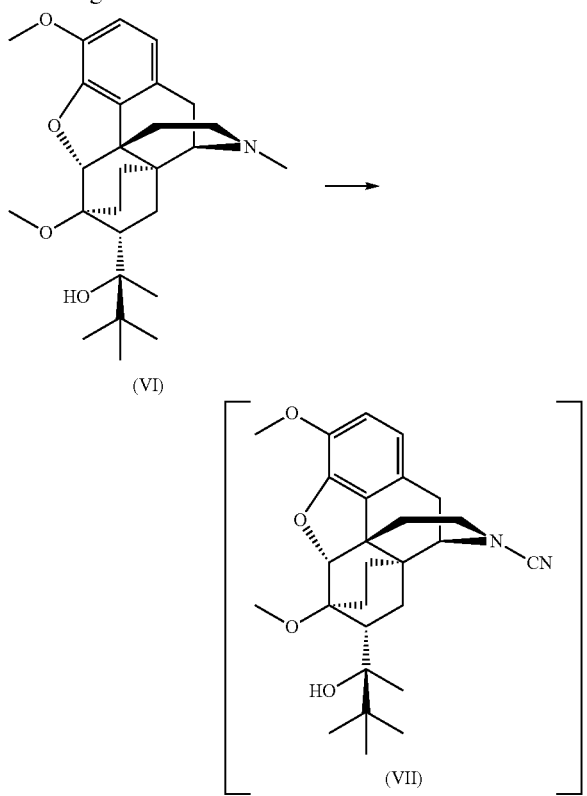

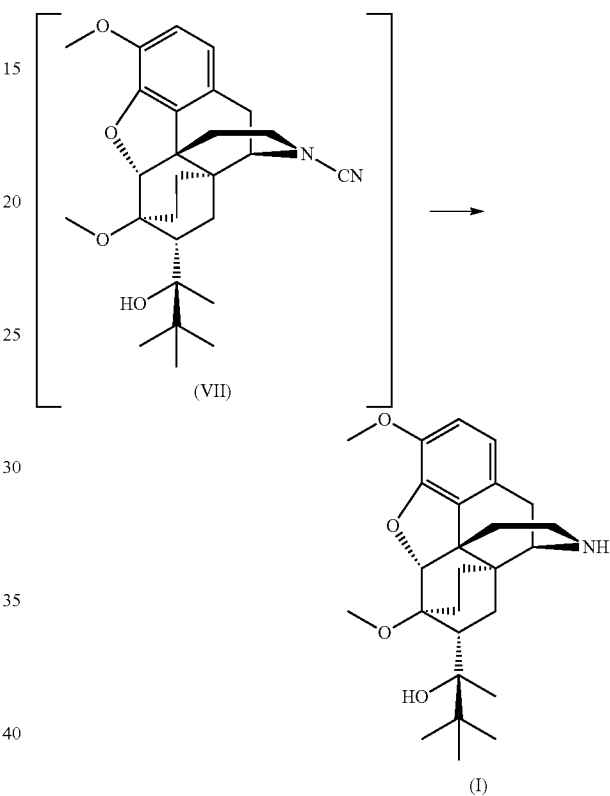

to provide a mixture that includes a compound of formula (VI), and wherein the hydrogenating step may optionally include the step of isolating the compound of formula (VI);

reacting the compound of formula (VI) with a source of cyanide in a first alcoholic solvent, as illustrated by the following schematic:

wherein the first alcoholic solvent includes one or more of a secondary alcohol and tertiary alcohol, and wherein the reaction of the compound of formula (VI) may optionally include a first inorganic base, to provide a mixture that includes a compound of formula (VII), and wherein the reacting step may optionally include the step of isolating the compound of formula (VII); and reacting the compound of formula (VII) with a second inorganic base in a second alcoholic solvent, as illustrated by the following schematic:

wherein the second alcoholic solvent includes one or more of a secondary alcohol and tertiary alcohol, and wherein the second alcoholic solvent may optionally be the same as the first alcoholic solvent, to provide a mixture that includes a compound of formula (I). In some embodiments, the compound of formula (I) may be isolated.

In some embodiments, the step of hydrogenating the compound of formula (V) includes hydrogenating the compound of formula (V) with hydrogen gas in the presence of a Palladium catalyst (e.g., Pd/C).

In some embodiments, the methyl vinyl ketone may be present in an amount of about 1 to about 10 molar equivalents.

In some embodiments, in the step of reacting the compound of formula (II), the solution may include toluene, a mixture of toluene and water, or a mixture of isopropyl alcohol and water.

In some embodiments, in the step of azeotropically removing water and/or an alcoholic solvent, water and/or alcoholic solvents are removed by azeotropic distillation.

In some embodiments, the Grignard reagent (e.g., t-butyl MgCl, t-butyl MgBr, or t-butyl MgI) is present in an amount of about 1.5 to about 15 molar equivalents.

In some embodiments, the Grignard reagent is t-butyl MgCl.

In some embodiments, in the step of reacting the anhydrous mixture of the compound formula (III) and the compound of formula (IV) with the Grignard reagent, the compound (III) and the compound of formula (IV) are added to the Grignard reagent (e.g., t-butyl MgCl, t-butyl MgBr, or t-butyl MgI) at a rate configured to maintain an internal reaction mixture temperature of less than about 15° C.

In some embodiments, the step of reacting the anhydrous mixture of the compound formula (III) and the compound of formula (IV) with the Grignard reagent further comprises quenching any unreacted Grignard reagent (e.g., t-butyl MgCl, t-butyl MgBr, or t-butyl MgI) with a solution of ammonium chloride and water.

In some embodiments, the step of isolating the compound of formula (V) comprises extracting the compound of formula (V) from the mixture that includes the compound of formula (V) with a mixture of water and acid, wherein the mixture of water and acid has a pH of less than about 3, to provide a first biphasic mixture that may be separated to provide an aqueous layer that includes the compound of formula (V).

In some embodiments, the step of isolating the compound of formula (V) comprises extracting the compound of formula (V) from the aqueous layer that includes the compound of formula (V) with a selected organic solvent to provide a second biphasic mixture; adjusting the pH of the second biphasic mixture to a pH of about pH 8 to about pH 12; separating the layers of the second, pH adjusted biphasic mixture to provide an organic layer that includes the compound of formula (V). In some embodiments, the acid may be sulfuric acid and the selected organic solvent may be isopropyl acetate.

In some embodiments, the compound of formula (VI) may be isolated.

In some embodiments, the source of cyanide includes cyanogen bromide and, in certain embodiments, includes cyanogen bromide in acetonitrile or cyanogen bromide in dichloromethane.

In some embodiments, the source of cyanide is present in an amount of about 1 to about 5 molar equivalents.

In some embodiments, the compound of formula (VI) is reacted with the source of cyanide where the reaction includes the first inorganic base. In some embodiments, the first inorganic base may be selected from the group consisting of sodium carbonate and potassium carbonate. In some embodiments, the first inorganic base is present in an amount of about 0.05 to about 1 molar equivalents.

In some embodiments, the first and/or second alcoholic solvent may be selected from the group consisting of 2-pentanol, 4-methyl-2-pentanol, cyclopentanol, cyclohexanol, 3-ethyl-3-pentanol, and 2-methyl-2-hexanol. In some embodiments, the first and/or second alcoholic solvent is selected from the group consisting of 4-methyl-2-pentanol and cyclopentanol.

In some embodiments, the process further comprises quenching the mixture that includes the compound of formula (VII) with water to provide a biphasic mixture, wherein the biphasic mixture may be separated to provide an organic layer that includes the compound of formula (VII).

In some embodiments, the second inorganic base may be selected from the group consisting of potassium hydroxide and sodium hydroxide.

In some embodiments, the second inorganic base may be present in an amount of about 1 to about 10 molar equivalents.

In some embodiments, the mixture that includes the compound of formula (I) may be extracted with water to provide a biphasic mixture that may be separated to provide an organic layer that includes the compound of formula (I).

In an embodiment, the invention includes a process for preparing buprenorphine, or a pharmaceutically acceptable salt thereof, the process including the step of hydrolyzing a compound of formula (I), prepared according to one or more of the processes described herein, to provide buprenorphine or a pharmaceutically acceptable salt thereof.

In an embodiment, the invention may include a process for preparing a compound of formula (I) or a pharmaceutically acceptable salt thereof, the process including the steps of:

reacting the compound of formula (VI) with a source of cyanide in a first alcoholic solvent, as illustrated by the following schematic:

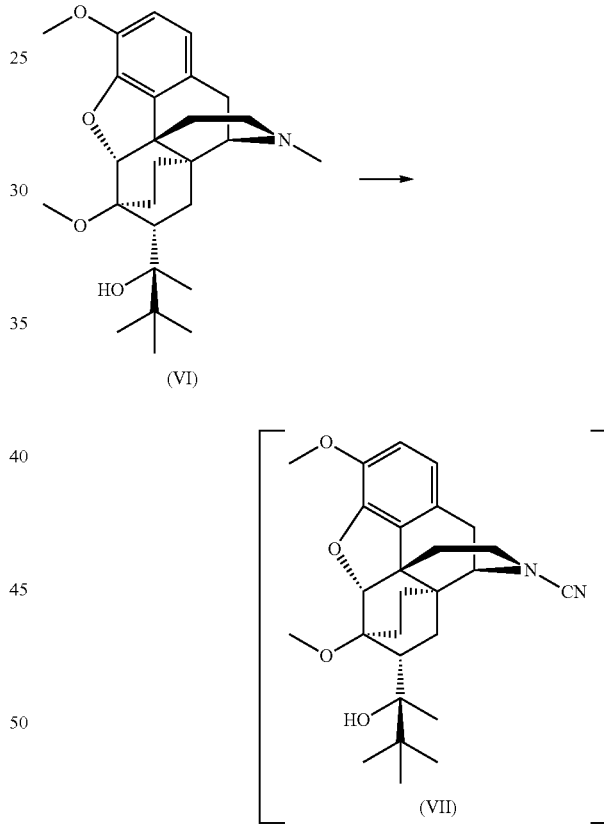

wherein the first alcoholic solvent includes one or more of a secondary alcohol and tertiary alcohol, and wherein the reaction of the compound of formula (VI) may optionally include a first inorganic base, to provide a mixture that includes a compound of formula (VII), wherein the compound of formula (VII) may not be isolated from the mixture that includes the compound of formula (VII); and reacting the compound of formula (VII) with a second inorganic base in a second alcoholic solvent, as illustrated by the following schematic:

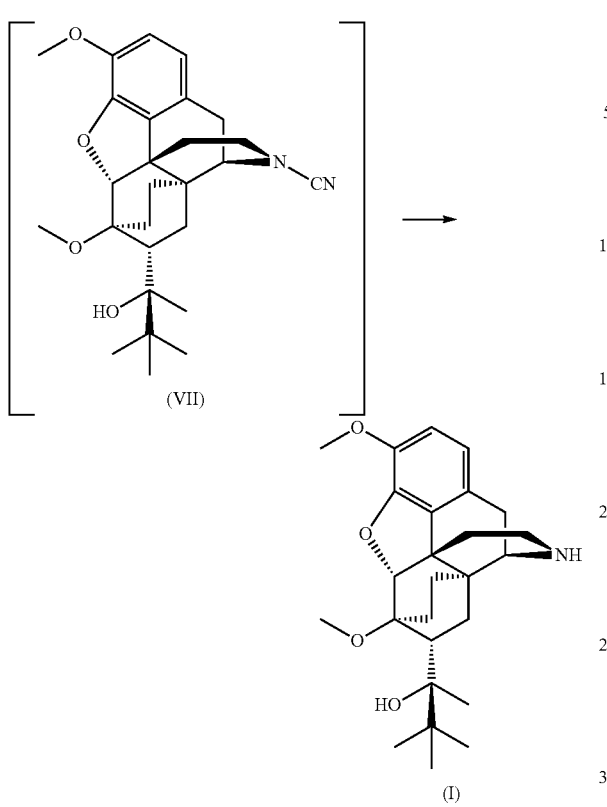

(VII)

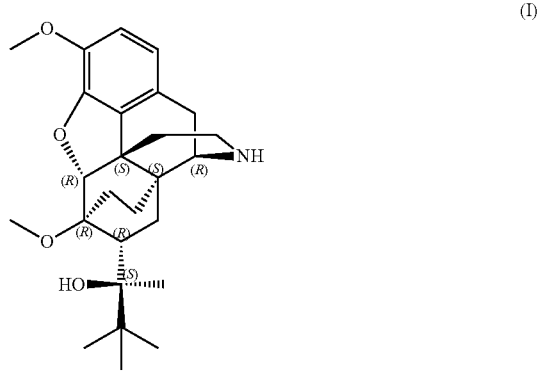

(I)

wherein the second alcoholic solvent includes one or more of a secondary alcohol and tertiary alcohol, and wherein the second alcoholic solvent may optionally be the same as the first alcoholic solvent, to provide a mixture that includes a compound of formula (I), wherein the compound of formula (I) may be optionally isolated from the mixture that includes the compound of formula (I). In some embodiments, the source of cyanide may be cyanogen bromide or, in certain embodiments, may be cyanogen bromide in acetonitrile or cyanogen bromide in dichloromethane. In some embodiments, the first and/or second alcoholic solvent may be a secondary alcohol. In some embodiments, the first and/or second alcoholic solvent may be selected from the group consisting of 2-pentanol, 4-methyl-2-pentanol, cyclopentanol, cyclohexanol, 3-ethyl-3-pentanol, and 2-methyl-2-hexanol. In some embodiments, the first and/or second alcoholic solvent may be selected from the group consisting of 4-methyl-2-pentanol and cyclopentanol. In some embodiments, the process includes the step of further reacting the compound of formula (I) to provide buprenorphine or a pharmaceutically acceptable salt thereof.

In an embodiment, the invention may be directed to a process for the preparation of a compound of formula (I):

(I)

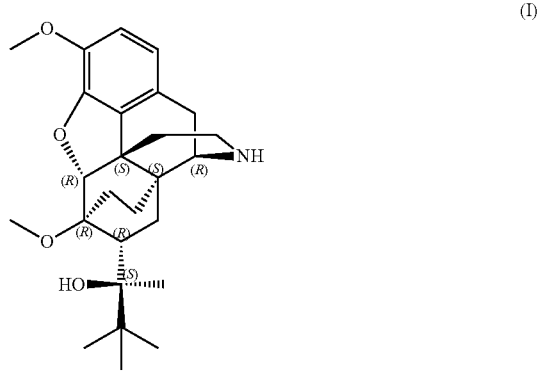

or a pharmaceutically acceptable salt thereof; comprising the steps of

Step 1:

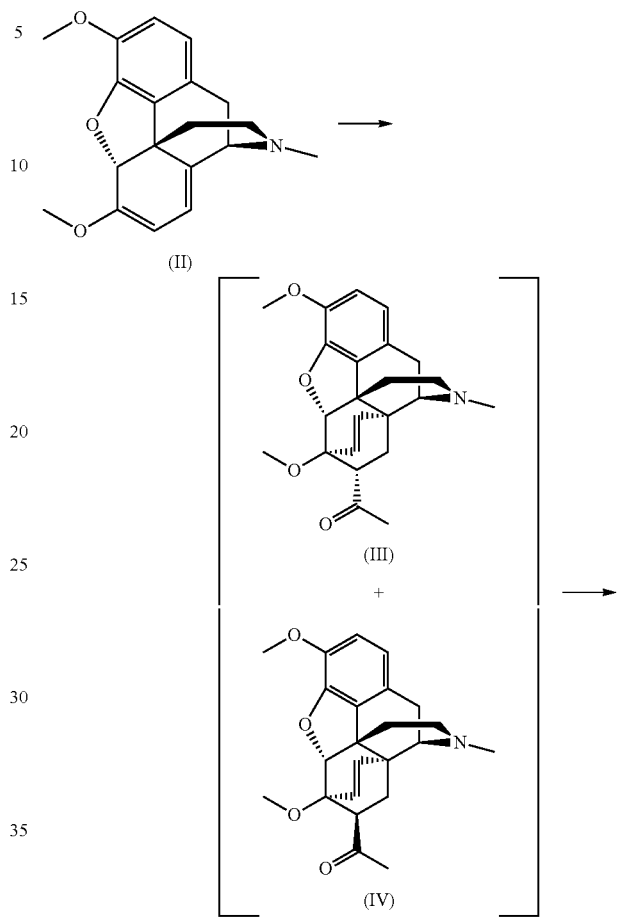

reacting thebaine, a compound of formula (II), with methyl vinyl ketone; in an organic solvent, mixture of organic solvents or mixture of water and one or more organic solvent(s); to yield a mixture comprising the corresponding compound of formula (III), the corresponding compound of formula (IV); wherein the compound of formula (III) and the compound of formula (IV) are not isolated;

Step 2:

azeotropically removing any water and any alcoholic solvents present in the mixture comprising the compound of formula (III) and the compound of formula (IV); to yield an anhydrous mixture comprising the compound of formula (III) and the compound of formula (IV);

Step 3:

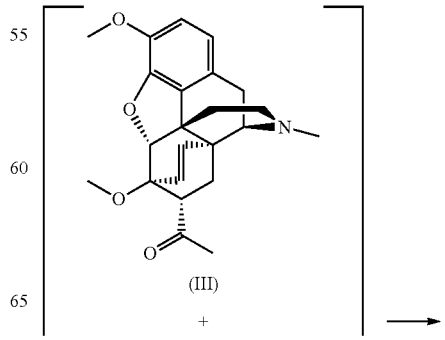

(III)

+

-continued

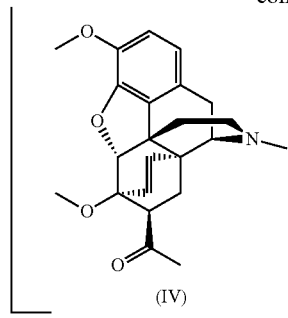

(IV)

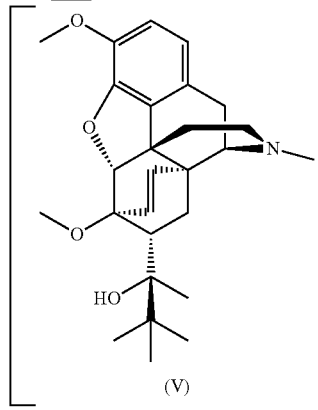

(V)

reacting the compound of formula (III) and the compound of formula (IV), present in the anhydrous mixture prepared in Step 2, with tert-butyl MgCl, tert-butyl MgBr or t-butyl MgI; under Grignard conditions; to yield a mixture comprising the corresponding compound of formula (V); wherein the compound of formula (V) is not isolated;

Step 4:

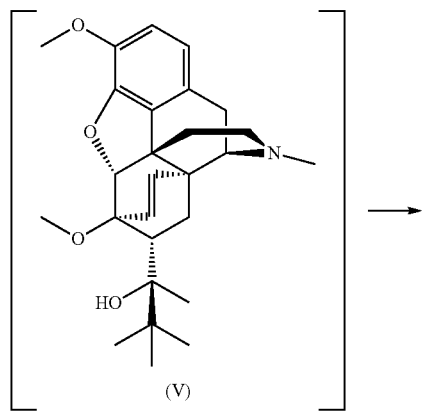

(V)

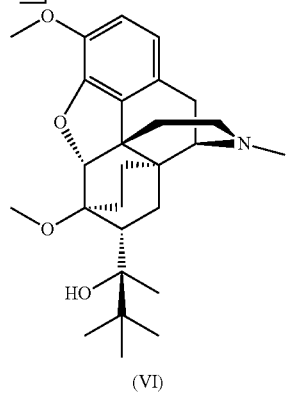

(VI)

hydrogenating the compound of formula (V); by reacting the compound of formula (V) with hydrogen gas; in the presence of a palladium catalyst; to yield a mixture comprising the corresponding compound of formula (VI); wherein the compound of formula (VI) is optionally isolated;

Step 5:

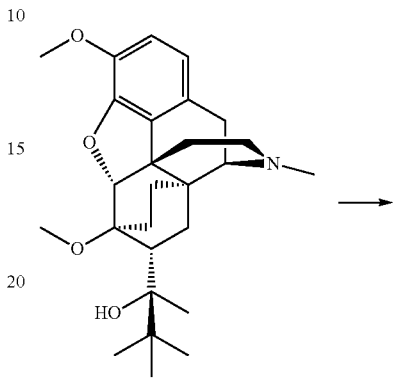

(VI)

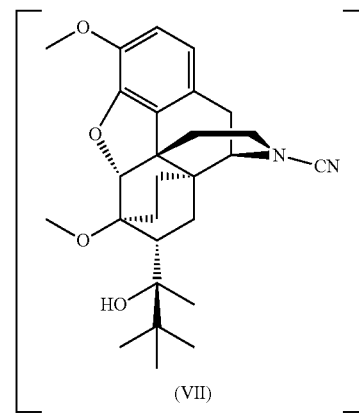

(VII)

reacting the compound of formula (VI) with a source of cyanide; optionally in the presence of an inorganic base; in a secondary or tertiary alcohol; to yield a mixture comprising the corresponding compound of formula (VII); wherein the compound of formula (VII) is not isolated; and Step 6:

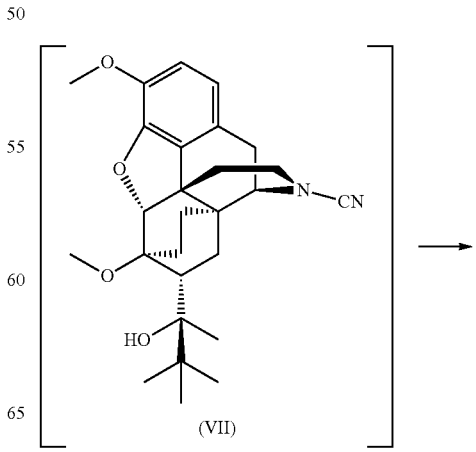

(VII)

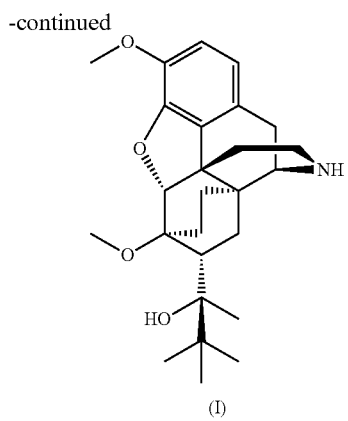

(I)

hydrolyzing the compound of formula (VII); by reacting the compound of formula (VII) with an inorganic base; in a second secondary or tertiary alcohol; wherein the secondary or tertiary alcohol of Step 6 is the same as the secondary or tertiary alcohol of Step 5; to yield a mixture comprising the corresponding compound of formula (I); wherein the compound of formula (I) is optionally isolated.

In an embodiment, the invention may be directed to a process for the preparation of buprenorphine or pharmaceutically acceptable salt thereof; comprising the following steps:

Step 1:

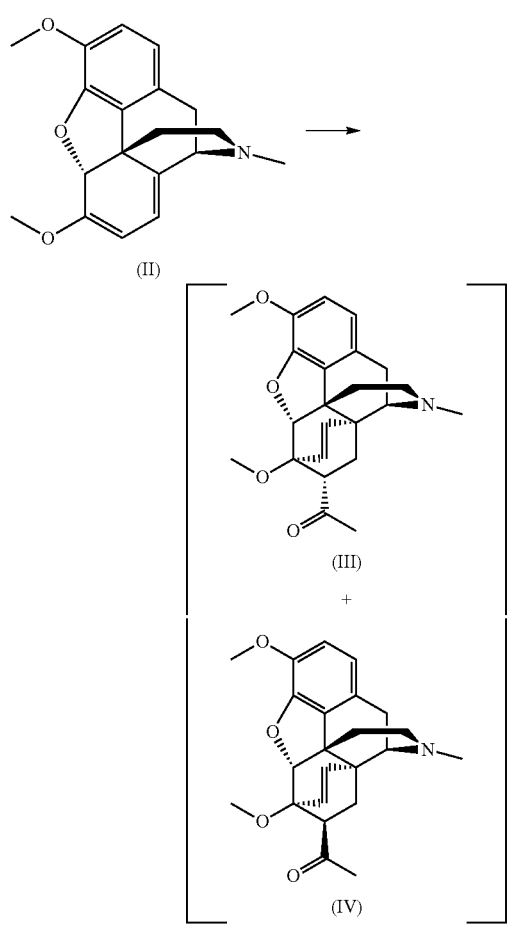

reacting thebaine, a compound of formula (II), with methyl vinyl ketone; in an organic solvent, mixture of organic solvents, or mixture of water and one or more organic solvent(s); to yield a mixture comprising the corresponding compound of formula (III), the corresponding compound of formula (IV); wherein the compound of formula (III) and the compound of formula (IV) are not isolated;

Step 2:

azeotropically removing any water and any alcoholic solvents present in the mixture comprising the compound of formula (III) and the compound of formula (IV); to yield an anhydrous mixture comprising the compound of formula (III) and the compound of formula (IV);

Step 3:

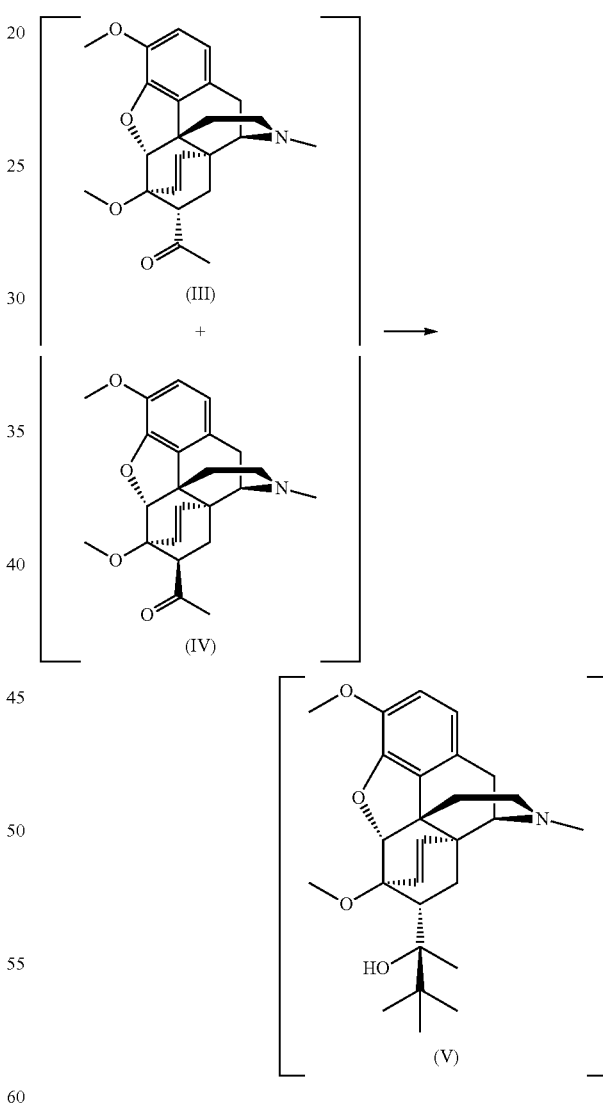

reacting the compound of formula (III) and the compound of formula (IV), present in the anhydrous mixture prepared in Step 2, with t-butyl MgCl, t-butyl MgBr, or t-butyl MgI; under Grignard conditions; to yield a mixture comprising the corresponding compound of formula (V); wherein the compound of formula (V) is not isolated;

Step 4:

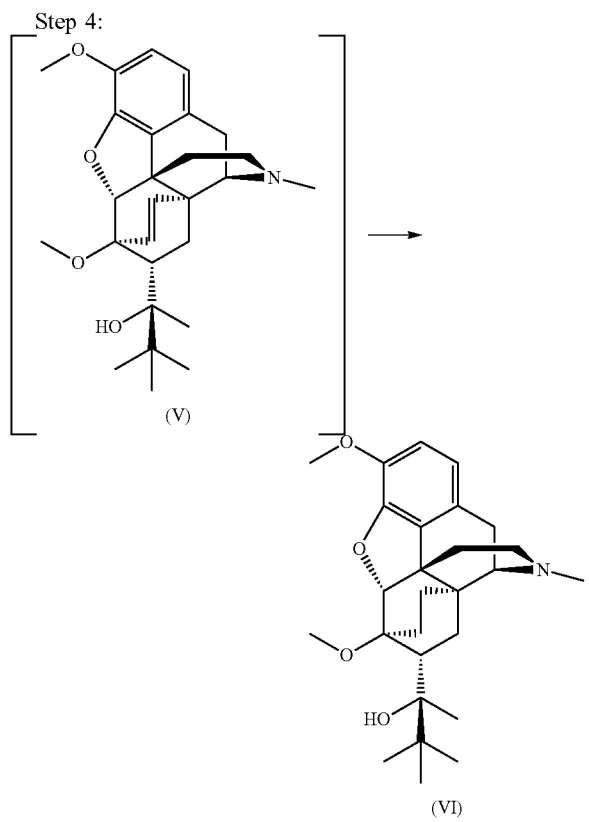

hydrogenating the compound of formula (V); by reacting the compound of formula (V) with hydrogen gas; in the presence of a palladium catalyst; to yield a mixture comprising the corresponding compound of formula (VI); wherein the compound of formula (VI) is optionally isolated;

Step 5:

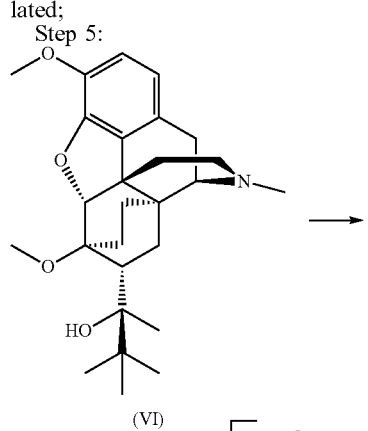

reacting the compound of formula (VI) with a source of cyanide; optionally in the presence of an inorganic base; in a secondary or tertiary alcohol; to yield a mixture comprising the corresponding compound of formula (VII); wherein the compound of formula (VII) is not isolated;

Step 6:

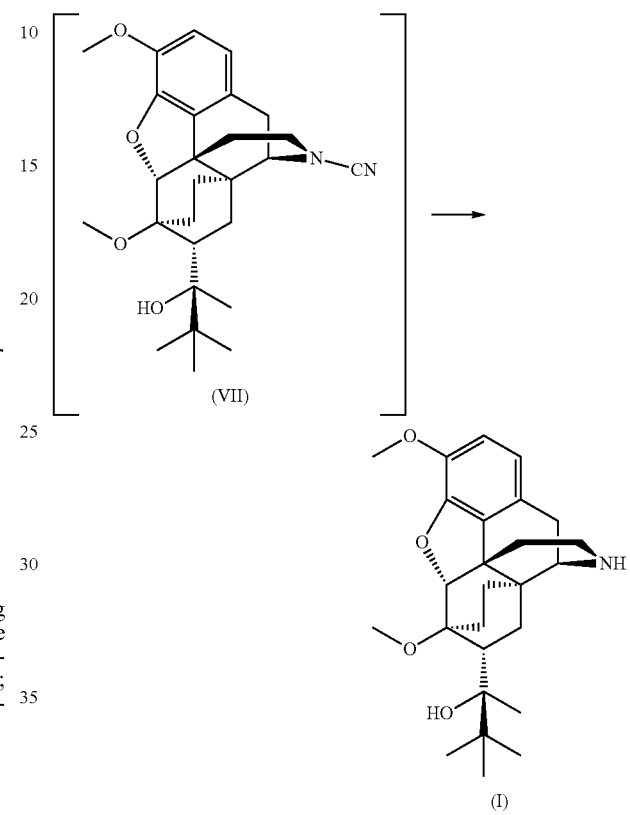

hydrolyzing the compound of formula (VII); by reacting the compound of formula (VII) with an inorganic base; in a secondary or tertiary alcohol; wherein the secondary or tertiary alcohol of Step 6 is the same as the secondary or tertiary alcohol of Step 5; to yield a mixture comprising the corresponding compound of formula (I); wherein the compound of formula (I) is optionally isolated; and Step 7:

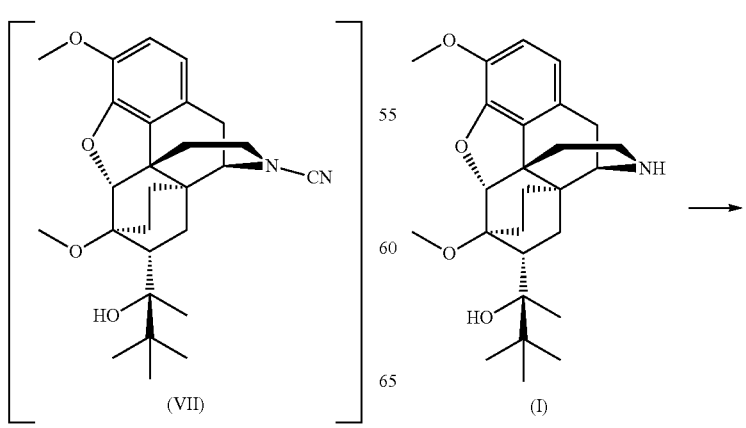

-continued

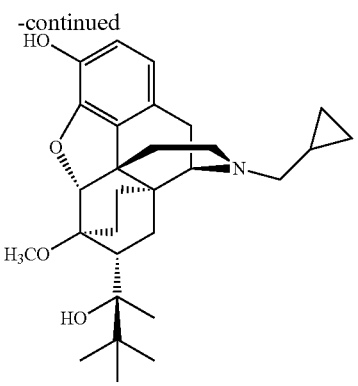

reacting the compound of formula (I) to yield buprenorphine or a pharmaceutically acceptable salt thereof (preferably a hydrochloride salt).

The invention may be further directed to a process for the preparation of a compound of formula (I):

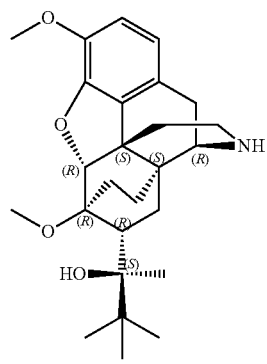

(I)

or a pharmaceutically acceptable salt thereof; comprising the steps of

Step A:

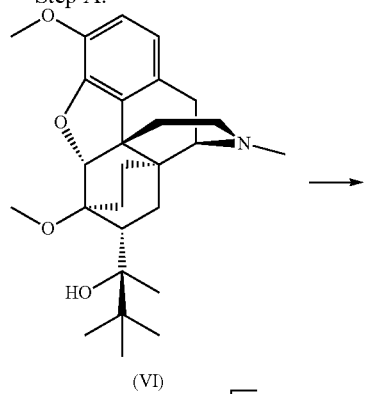

(VI)

reacting a compound of formula (VI) with a source of cyanide; optionally in the presence of an inorganic base; in a secondary or tertiary alcohol; to yield a mixture comprising the corresponding compound of formula (VII); wherein the compound of formula (VII) is not isolated; and Step B:

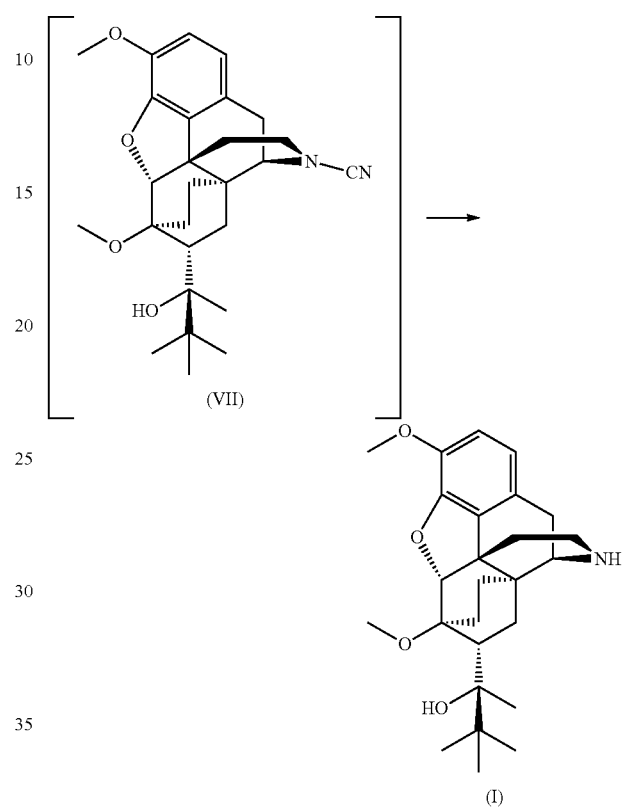

reacting the compound of formula (VII) with an inorganic base; in a secondary or tertiary alcohol; wherein the secondary or tertiary alcohol of Step A is the same as the secondary or tertiary alcohol of Step B; to yield a mixture comprising the corresponding compound of formula (I); wherein the compound of formula (I) is optionally isolated.

In an embodiment, the invention may be directed to a process for the preparation of buprenorphine or a pharmaceutically acceptable salt thereof, comprising the steps of:

Step A:

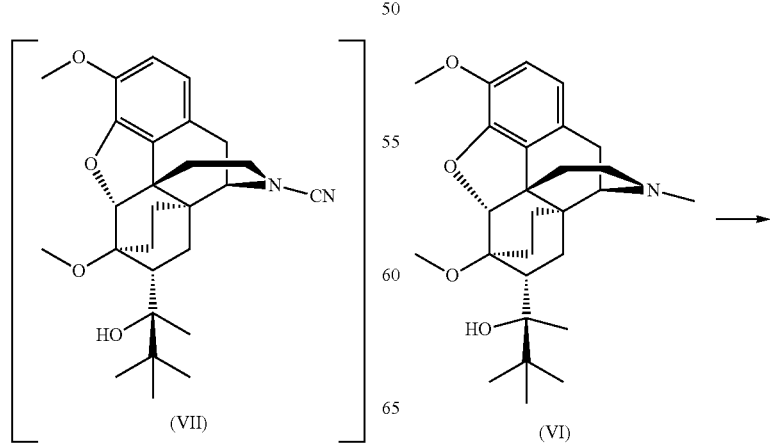

-continued

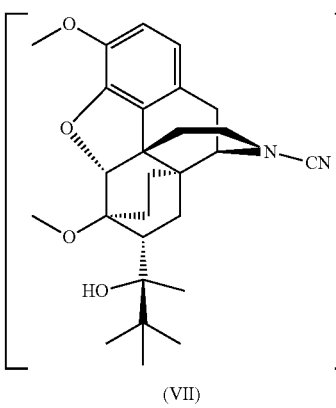

(VII)

reacting a compound of formula (VI) with a source of cyanide; optionally in the presence of an inorganic base; in a secondary or tertiary alcohol; to yield the corresponding compound of formula (VII); wherein the compound of formula (VII) is not isolated; and Step B:

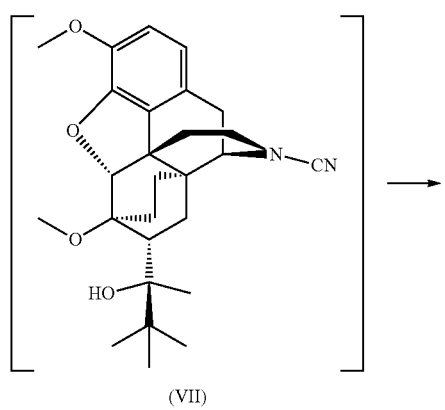

(VII)

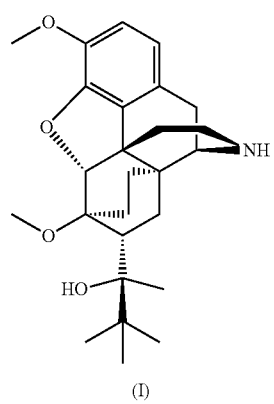

(I)

reacting the compound of formula (VII) with an inorganic base; in a secondary or tertiary alcohol; wherein the secondary or tertiary alcohol of Step A is the same as the secondary or tertiary alcohol of Step B; to yield the corresponding compound of formula (I); wherein the compound of formula (I) is optionally isolated; and Step C:

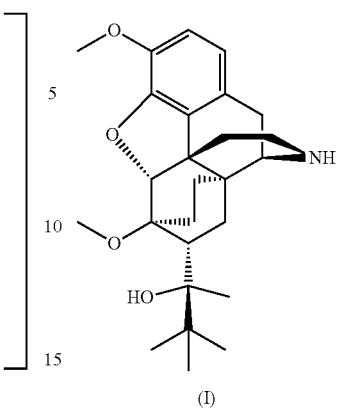

(I)

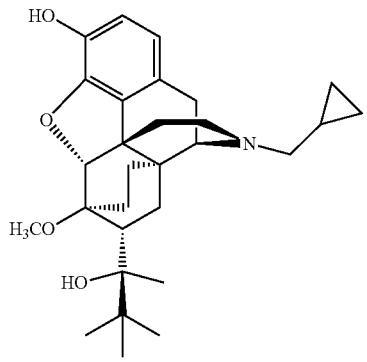

reacting the compound of formula (I) to yield buprenorphine or a pharmaceutically acceptable salt thereof (preferably a hydrochloride salt).

The invention may be further directed to a process for the preparation of a compound of formula (VI):

(VI)

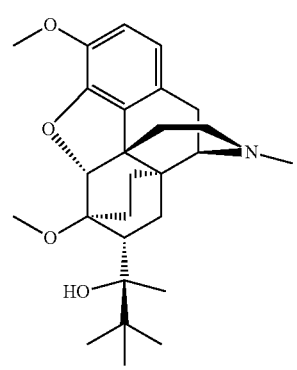

or a pharmaceutically acceptable salt thereof, comprising the steps of:

Step 1:

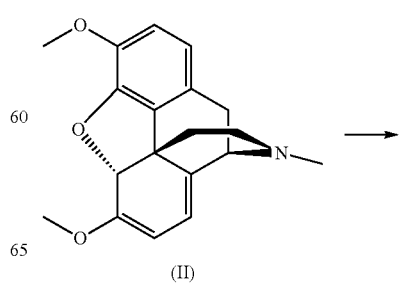

(II)

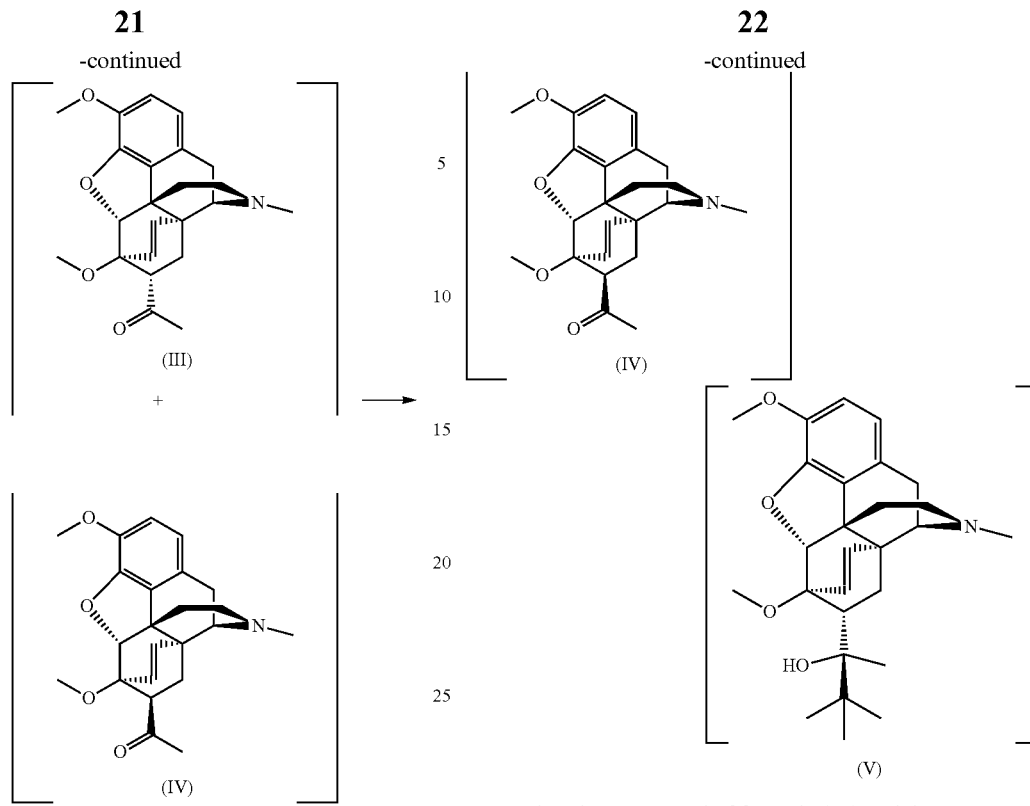

reacting thebaine, a compound of formula (II), with methyl vinyl ketone; in an organic solvent, mixture of organic solvents or mixture of water and one or more organic solvent(s); to yield a mixture comprising the corresponding compound of formula (III), the corresponding compound of formula (IV); wherein the compound of formula (III) and the compound of formula (IV) are not isolated;

Step 2:

azeotropically removing any water and any alcoholic solvents present in the mixture comprising the compound of formula (III) and the compound of formula (IV); to yield an anhydrous mixture comprising the compound of formula (III) and the compound of formula (IV);

Step 3:

reacting the compound of formula (III) and the compound of formula (IV), present in the anhydrous mixture prepared in Step 2, with tert-butyl MgCl, tert-butyl MgBr, or t-butyl MgI; under Grignard conditions; to yield a mixture comprising the corresponding compound of formula (V); wherein the compound of formula (V) is not isolated; and Step 4:

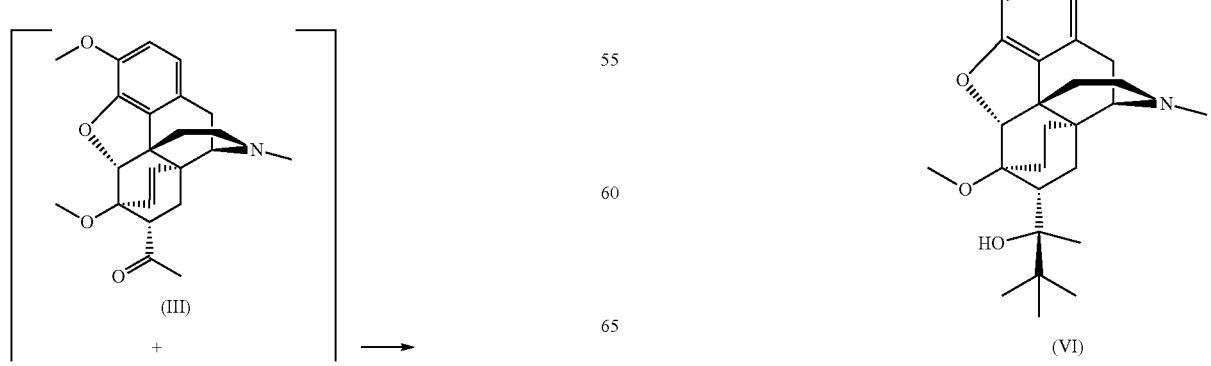

hydrogenating the compound of formula (V); by reacting the compound of formula (V) with hydrogen gas; in the presence of a palladium catalyst; to yield a mixture comprising the corresponding compound of formula (VI); wherein the compound of formula (VI) is optionally isolated.

The invention may be further directed to any of the process(es) or combination of reaction steps that may be described herein.

The invention may be further directed to a product prepared according to any of the process(es) described herein.

Illustrative of the invention is a pharmaceutical composition comprising a pharmaceutically acceptable carrier and buprenorphine or a pharmaceutically acceptable salt thereof, prepared according to any of the processes described herein. An illustration of the invention is a pharmaceutical composition made by mixing buprenorphine or a pharmaceutically acceptable salt thereof, prepared according to any of the processes described herein, and a pharmaceutically acceptable carrier. Illustrating the invention is a process for making a pharmaceutical composition comprising mixing buprenorphine, or a pharmaceutically acceptable salt thereof, prepared according to any of the processes described herein and a pharmaceutically acceptable carrier.

Exemplifying the invention are methods for the treatment of pain (for example moderate or severe pain), where such methods comprise administering to a subject in need thereof a therapeutically effective amount of any of the products or pharmaceutical compositions described herein.

In an embodiment, the invention may be directed to buprenorphine or a pharmaceutically acceptable salt thereof, prepared according to any of the processes described herein for use as a medicament. In another embodiment, the invention may be directed to buprenorphine or a pharmaceutically acceptable salt thereof, prepared according to any of the processes described herein for use in the treatment of pain (for example, moderate or severe pain). In another embodiment, the invention may be directed to a composition comprising buprenorphine or a pharmaceutically acceptable salt thereof, prepared according to any of the processes described herein for the treatment of pain (for example, moderate or severe pain).

Another example of the invention is the use of buprenorphine or a pharmaceutically acceptable salt thereof, prepared according to any of the processes described herein in the preparation of a medicament for treating pain (for example, moderate or severe pain), in a subject in need thereof. In another example, the invention may be directed to buprenorphine or a pharmaceutically acceptable salt thereof, prepared according to any of the processes described herein for use in a method for treating pain (for example, moderate or severe pain), in a subject in need thereof.

DETAILED DESCRIPTION OF THE INVENTION

In certain embodiments, the invention is directed to processes for the preparation of (S)-2((4R,4aS,6R,7R,7aR,12bS)-7,9-dimethoxy-1,2,3,4,5,6,7,7a-octahydro-4a,7-ethano-4,12-methanobenzofuro[3,2-e]isoquinolin-6-yl)-3,3-dimethylbutan-2-ol, a compound of formula (I):

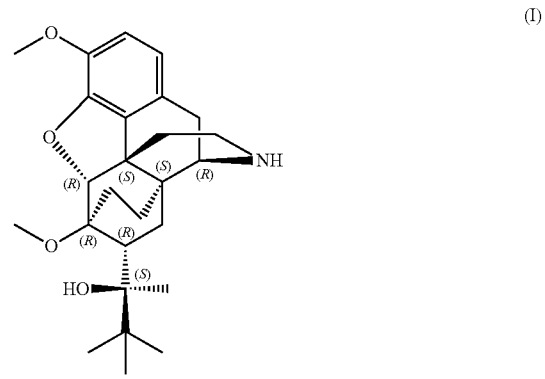

and pharmaceutically acceptable salts thereof, which are useful in the synthesis of buprenorphine, an opioid useful for the treatment of pain (for example, moderate or severe pain), opioid addiction, alcohol addiction, opioid detoxification and/or counteracting opioid overdose; or are useful as intermediates in the synthesis of compounds useful for the treatment of pain. The invention may be further directed to processes for the preparation of buprenorphine, its intermediates, or a pharmaceutically acceptable salt thereof, as described herein.

The process(es) of the invention are advantageous over previously described processes for the preparation of the compound of formula (I) and/or buprenorphine, or a pharmaceutically salt thereof, because said process(es) require fewer intermediate isolations, resulting in an improvement in yield and/or purity. The process(es) of the invention are additionally more cost-effective, use solvents which are environmentally "friendly" (e.g., non-toxic) and/or use solvents which do not require special handling in manufacture.

Abbreviations used in the specification, particularly the Schemes and Examples, are as follows:
CPS Thebaine=Concentrate of poppy straw, thebaine
DCM=Dichloromethane
17,18-DHBU3=17,18-dihydro derivative of BU3 (which may be present as an α-isomer, as a β-isomer or mixture thereof)
HPLC=High Performance Liquid Chromatography
IPAc=Isopropyl Acetate
2-methyl THF=2-Methyl-tetrahydrofuran
Pd—C or Pd/C=Palladium on carbon (catalyst)
t-Bu or tert-Bu=tert-Butyl
THF=Tetrahydrofuran As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the invention. In certain embodiments, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Some of the crystalline forms for the compounds of the invention may exist as polymorphs and as such are intended to be included in the invention. In addition, some of the compounds of the invention may form solvates with water (i.e., hydrates) or common organic solvents, and such solvates are also intended to be encompassed within the scope of this invention.

It is intended that within the scope of the invention, any element, in particular when mentioned in relation to a compound of formula (I), shall comprise all isotopes and isotopic mixtures of said element, either naturally occurring or synthetically produced, either with natural abundance or in an isotopically enriched form. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O. The isotopes may be radioactive or non-radioactive. Radiolabelled compounds of formula (I) may comprise a radioactive isotope selected from the group consisting of $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^3$H, $^{11}$C and $^{18}$F.

As used herein, unless otherwise noted, the term "substantially pure form" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment, the invention is directed to a process wherein the compound of formula (I) is prepared as a substantially pure form. In another embodiment, the invention is directed to a process wherein the compound of formula (II) is prepared as a substantially pure form.

As used herein, unless otherwise noted, the term "substantially free of a corresponding salt form(s)" when used to described the compound of formula (I) shall mean that the mole percent of the corresponding salt form(s) in the isolated base of formula (I) is less than about 5 mole percent, preferably less than about 2 mole percent, more preferably, less than about 0.5 mole percent, most preferably less than about 0.1 mole percent. In an embodiment, the invention is directed to a process wherein the compound of formula (I) is prepared in a form which is substantially free of corresponding salt form(s). In another embodiment, the invention is directed to a process wherein the compound of formula (II) is prepared in a form which is substantially free of corresponding salt form(s).

As used herein, unless otherwise noted, the terms "treating," "treatment" and the like, shall include the management and care of a subject or patient (preferably mammal, more preferably human) for the purpose of combating a disease, condition, or disorder and includes the administration of a compound of the invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) the delay or avoidance of the development of the disorder or condition.

One skilled in the art will recognize that wherein the invention is directed to methods of prevention, a subject in need thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease, or condition to be prevented, but who has been deemed by a physician, clinician, or other medical profession to be at risk of developing said disorder, disease, or condition. For example, the subject may be deemed at risk of developing a disorder, disease, or condition (and therefore in need of prevention or preventive treatment) as a consequence of the subject's medical history, including, but not limited to, family history, pre-disposition, co-existing (co-morbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of an active compound (e.g., buprenorphine) or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

To provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic base as a reagent, the organic base selected for the first step may be the same or different than the organic base of the second step. Further, one skilled in the art will recognize that wherein a reaction step of the invention may be carried out in a variety of solvents or solvent systems, said reaction step may also be carried out in a mixture of the suitable solvents or solvent systems. One skilled in the art will further recognize that wherein two consecutive reaction or process steps are run without isolation of the intermediate product (i.e., the product of the first of the two consecutive reaction or process steps), then the first and second reaction or process steps may be run in the same solvent or solvent system; or alternatively may be run in different solvents or solvent systems following solvent exchange, which may be completed according to known methods.

Examples of suitable solvents, bases, reaction temperatures, and other reaction parameters and components are provided in the detailed description which follows herein. One skilled in the art will recognize that the listing of said examples is not intended, and should not be construed, as limiting in any way the invention set forth in the claims which follow thereafter.

During any of the processes for preparation of the compounds of the invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is, for example, methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

As used herein, unless otherwise noted, the term "oxygen protecting group" shall mean a group which may be attached to an oxygen atom to protect said oxygen atom from participating in a reaction and which may be readily removed following the reaction. Suitable oxygen protecting groups include, but are not limited to, acetyl, benzoyl, t-butyl-dimethylsilyl, trimethylsilyl (TMS), MOM, THP, and the like. Other suitable oxygen protecting groups may be found in texts such as T. W. Greene & P. G. M. Wuts, *Protective Groups in Organic Synthesis*, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows:

$$[(Rmoles-Smoles)/(Rmoles+Smoles)]\times 100\%$$

where Rmoles and Smoles are the R and S mole fractions in the mixture such that Rmoles+Smoles=1. The enantiomeric excess may alternatively be calculated from the specific rotations of the desired enantiomer and the prepared mixture as follows:

$$ee=([\alpha-obs]/[\alpha-max])\times 100.$$

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)(1S)-camphor-10-sulfonic acid, capric acid, caproic acid, caprylic acid, cinnamic acid, citric acid, cyclamic acid, dodecylsulfuric acid, ethane-1,2- disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

In some embodiments, the compositions of the invention may include a "pharmaceutically acceptable carrier" or "pharmaceutically acceptable excipient" or "physiologically compatible" carrier or carrier medium is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art.

Process Details

In an embodiment, the invention is directed to processes for the preparation of (S)-2((4R,4aS,6R,7R,7aR,12bS)-7,9-dimethoxy-1,2,3,4,5,6,7,7a-octahydro-4a,7-ethano-4,12-methanobenzofuro[3,2-e]isoquinolin-6-yl)-3,3-dimethylbutan-2-ol, as described in more detail in Scheme 1, below.

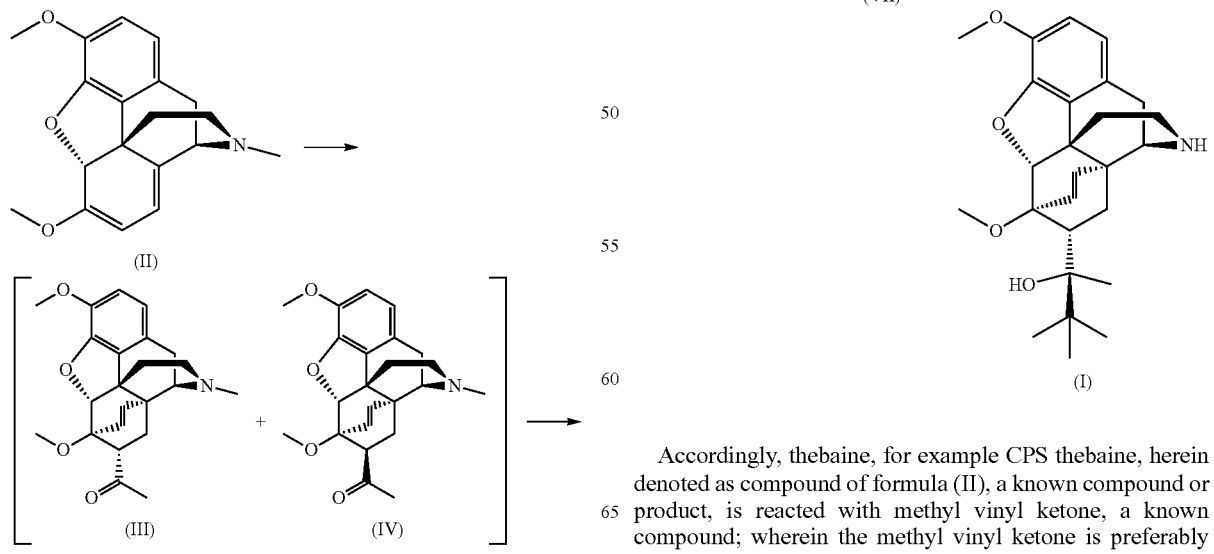

Accordingly, thebaine, for example CPS thebaine, herein denoted as compound of formula (II), a known compound or product, is reacted with methyl vinyl ketone, a known compound; wherein the methyl vinyl ketone is preferably present in an amount in the range of from about 1 to about 10 molar equivalents, preferably, in an amount in the range of from about 1.5 to about 5 molar equivalents, preferably, in an amount in the range of from about 2 to 10 about 4 molar equivalents, more preferably, in an amount of about 2.2 molar equivalents.

In a suitably selected organic solvent, a mixture of organic solvents or a mixture of water and one or more organic solvent(s), such as methanol, ethanol, isopropanol, toluene, THF, 2-methyl-THF, acetonitrile, ethyl acetate, isopropyl acetate, a mixture of water and toluene, a mixture of water and isopropyl alcohol, and the like, preferably a mixture of water and an organic solvent, more preferably, toluene or a mixture of water and isopropyl alcohol, more preferably a mixture of water and isopropyl alcohol wherein the isopropyl alcohol is present in an amount in the range of from about 10% to about 50% by volume, more preferably a mixture of water and isopropyl alcohol wherein the isopropyl alcohol is present in an amount in the range of from about 25% to about 30% by volume; optionally under a nitrogen atmosphere; at a temperature in the range of from about 60° C. to about 95° C., preferably at a temperature in the range of from about 75° C. to about 90° C.; more preferably at a temperature of about 84° C.; to yield a mixture comprising the corresponding alpha isomer, the compound of formula (III) and the corresponding beta isomer, the compound of formula (IV), which compounds are not isolated.

To the mixture comprising the compound of formula (III) and the compound of formula (IV) is optionally added a suitably selected organic solvent such as toluene, and the like.

The mixture comprising the compound of formula (III) and the compound of formula (IV) is heated under distillation conditions, to azeotropically remove any water (including for example any water which was introduced with the thebaine) and any alcoholic solvents that may be present in the mixture; to yield an anhydrous mixture comprising the organic solvent (e.g. toluene), the compound of formula (III) and the compound of formula (IV). The compound of formula (III) and the compound of formula (IV) are not isolated, either individually or as a mixture.

One skilled in the art will recognize that the distillation is continued until all residual water and, where present, alcoholic solvent is removed from the mixture, which endpoint may be determined by for example, the reflux temperature of the mixture. Preferably, the mixture is subjected to distillation until the reflux temperature reaches about 114-115° C.

The anhydrous mixture comprising the compound of formula (III) and the compound of formula (IV) (prepared in Pot 1/Step 1 as described herein) is reacted with t-butyl MgCl, t-butyl-MgBr or t-butyl-MgI; wherein the t-butyl MgCl, t-butyl-MgBr or t-butyl-MgI is preferably present in an amount in the range of from about 1.5 to about 15 molar equivalents (relative to the molar amount of thebaine), preferably, in an amount in the range of from about 3.5 to about 10 molar equivalents, preferably, in an amount in the range of from about 5 to about 10 molar equivalents, preferably, in an amount in the range of from about 7.5 to about 10 molar equivalents, more preferably, in an amount of about 8 to about 9.5 molar equivalents; preferably, at a temperature in the range of from about −78° C. to about room temperature, preferably, at a temperature in the range of from about −25° C. to about room temperature, more preferably at a temperature in the range of about 0° C. to about 15° C., more preferably, at a temperature in the range of from about 5° C. to about 10° C.; to yield a mixture comprising the corresponding compound of formula (V). The compound of formula (V) is not isolated.

Preferably, the anhydrous mixture comprising the compound of formula (III) and the compound of formula (IV) (prepared in Pot 1/Step 1) is added to the anhydrous mixture comprising t-butyl MgCl, t-butyl-MgBr or t-butyl-MgI (the Grignard reagent), and a suitably selected anhydrous organic solvent or mixture of anhydrous organic solvents such as THF, cyclohexane, toluene, heptane, and the like, preferably a mixture of THF and cyclohexane, more preferably in a ratio of about 1:2 to about 1:4 ratio volume:volume of THF:cyclohexane, more preferably in a ratio of about 1:3 to about 1:4 volume:volume THF:cyclohexane.

Preferably, the addition of the mixture comprising the compound of formula (III) and the compound of formula (IV) into the mixture comprising t-butyl-MgCl, t-butyl-MgBr or t-butyl-MgI (the Grignard reagent) is controlled to a rate of addition which maintains the internal temperature of the reaction mixture below about 15° C., preferably at a temperature of about 8-10° C.

One skilled in the art will recognize that the t-butyl MgCl, t-butyl-MgBr or t-butyl-MgI Grignard reagent may be prepared according to known methods. For example, 2-chloro-2-methylpropane (or 2-bromo-2-methylpropane or 2-iodo-2-methylpropane), a known compound, in a suitably selected anhydrous organic solvent or mixture of anhydrous organic solvents such as cyclohexane; is added to a magnesium (e.g. magnesium shavings) suspension; wherein the magnesium is suspended in a suitably selected anhydrous organic solvent or mixture of anhydrous organic solvents such as a mixture of THF and cyclohexane; at a temperature in the range of from about 60° C. to about 75° C.

Preferably, the mixture comprising the compound of formula (V) is quenched according to known methods. For example, the reaction mixture (which in addition to the compound of formula (V) may further contain unreacted Grignard reagent) is quenched by addition of a solution of ammonium chloride in water; preferably, in an amount sufficient to consume any unreacted magnesium, as would be readily determined by one skilled in the art.

Preferably, the mixture comprising the compound of formula (V) is extracted with a mixture of water and a suitably selected acid such as sulfuric acid, hydrochloric acid, acetic acid, and the like, preferably sulfuric acid; preferably with a suitably selected aqueous acid mixture at a pH less than about pH 5, more preferably at a pH less than about 3, more preferably in the range of from about pH 2.5 to about pH 1, more preferably an aqueous acid mixture at a pH of about 1; with the resulting biphasic mixture separated and the organic layer discarded. (One skilled in the art will recognize that that the compound of formula (V) will remain in the aqueous layer, whereas the organic layer, which contains any extracted organic impurities, is removed and discarded).

To the resulting aqueous layer, which comprises the compound of formula (V), is added a suitably selected organic solvent such as IPAc, ethyl acetate, and the like, preferably IPAc; and the pH of the resulting mixture adjusted to a pH greater than about pH 8, preferably to a pH in the range of from about pH 8 to about pH 12, more preferably to a pH in the range of from about pH 9 to about pH 11, more preferably to a pH of about 10. The resulting biphasic mixture is separated, the aqueous layer is discarded and the organic layer, comprising the compound of formula (V) taken into the next step of the process.

The compound of formula (V) is subjected to hydrogenation, for example, by reacting with hydrogen gas in the presence of a suitably selected catalyst, preferably a palladium catalyst, such as Pd/C, and the like, more preferably Pd/C; wherein the hydrogen gas is present at a pressure in the range of from about 30 psi to about 100 psi, preferably at a pressure in the range of from about 50 psi to about 75 psi; more preferably at a pressure of about 60-65 psi; at a temperature in the range of from about 40° C. to about 100° C., preferably at a temperature in the range of from about 50° C. to about 80° C., more preferably, at a temperature of about 60-70° C.; to yield a mixture comprising the corresponding compound of formula (VI).

Preferably, the compound of formula (VI) is isolated according to known methods, for example by evaporation, precipitation, crystallization, and the like, more preferably by hot filtration of the catalyst, evaporation of the solvent (to yield a residue comprising the compound of formula (VI)) and crystallization of the compound of formula (VI) from a suitably selected organic solvent such as methanol, ethanol, isopropyl alcohol, acetonitrile, and the like, preferably ethanol.

The compound of formula (VI) is reacted with a suitably selected source of cyanide, such as cyanogen bromide in a suitably selected organic solvent, such as a solution of cyanogen bromide in acetonitrile, cyanogen bromide in methylene chloride, and the like, preferably cyanogen bromide in acetonitrile; wherein the suitably selected source of cyanide is present in an amount in the range of from about 1 to about 5 molar equivalents (relative to the moles of the compound of formula (VI)), preferably in an amount in the range of from about 1.1 to about 3 molar equivalents, for example in an amount in the range of from about 1.2 to about 2 molar equivalents, more preferably in an amount of about 1.4 molar equivalents; and optionally in the presence of a suitably selected inorganic base such as sodium carbonate, potassium carbonate, sodium bicarbonate, and the like, preferably the inorganic base is sodium carbonate; wherein the inorganic base is optionally present in an amount in the range of from about 0.05 to about 1 molar equivalents (relative to the moles of the compound of formula (VI)), preferably in an amount in the range of from about 0.1 to about 0.75 molar equivalents, more preferably, in an amount in the range of from about 0.25 to about 0.5 molar equivalents, more preferably in an amount of about 0.4 molar equivalents; and in a suitably selected organic solvent (preferably, an organic solvent which is inert to cyanogen bromide, which is of sufficiently high boiling point as to be suitable for use in the subsequent hydrolysis step, and which preferably is not highly miscible with water), such as isopropyl acetate, DMF or a secondary or tertiary alcohol, preferably a suitably selected secondary or tertiary alcohol, (wherein the secondary alcohol is for example, 2-propanol, 2-butanol, 2-pentanol, 4-methyl-2-propanol, cyclopentanol, cyclohexanol, and the like; and wherein the tertiary alcohol is for example 3-ethyl-3-pentanol, 2-methyl-2-hexanol, 2-methyl-2-butanol, tert-butanol, and the like), preferably a secondary or tertiary alcohol such as 2-pentanol, 4-methyl-pentanol, cyclopentanol, cyclohexanol, 3-ethyl-3-pentanol, 2-methyl-2-hexanol, and the like, preferably a secondary alcohol such as 4-methyl-2-pentanol, cyclopentanol, cyclohexanol, and the like, preferably cyclopentanol; at a temperature in the range of from about room temperature to about reflux temperature, preferably at a temperature in the range of from about 25° C. to about 60° C., more preferably, at a temperature in the range of from about 30° C. to about 45° C., more preferably, at a temperature of about 45° C.; to yield a mixture comprising the corresponding compound of formula (VII). The compound of formula (VII) is not isolated.

Preferably, the mixture comprising the compound of formula (VII) is quenched with water, and the resulting biphasic mixture separated. The bottom, aqueous layer (comprising, for example, reaction impurities), is discarded. The top, organic layer, comprising the compound of formula (VII) is retained.

One skilled in the art will recognize that the use of a low density secondary or tertiary alcohol as the solvent for the reaction of the compound of formula (VI) with cyanogen bromide is particularly advantageous for manufacturing-scale separation of the aqueous layer, as the organic layer becomes the top layer, allowing easy removal of the undesired aqueous layer from the reactor.

Preferably, the mixture comprising the compound of formula (VII) is distilled (for example under vacuum) to remove any acetonitrile or methylene chloride which is introduced into in the reaction mixture with the cyanogen bromide), and further to remove any excess or unreacted cyanogen bromide.

The compound of formula (VII) is reacted (hydrolyzed) with a suitably selected inorganic base such as potassium hydroxide, sodium hydroxide, and the like, preferably potassium hydroxide; wherein the inorganic base is present in an amount in the range of from about 1 to about 10 molar equivalents (relative to the moles of the compound of formula (VII)), preferably in an amount in the range of from about 1 to about 6 molar equivalents, more preferably, in an amount in the range of from about 2 to about 4 molar equivalents, more preferably in an amount of about 3 molar equivalents; and in a suitably selected organic solvent, such as a secondary or tertiary alcohol (wherein the secondary alcohol is for example, 2-pentanol, 4-methyl-2-pentanol, cyclopentanol, cyclohexanol, and the like; and wherein the or tertiary alcohol is for example, 3-ethyl-3-pentanol, 2-methyl-2-hexanol, and the like), preferably a secondary alcohol, more preferably a secondary alcohol which is not substantially miscible with water, such as 4-methyl-pentanol, cyclopentanol, cyclohexanol, and the like, more preferably, cyclopentanol; and wherein the organic solvent for the reaction of the compound of formula (VII) is preferably the same as the organic solvent used in the reaction of the compound of formula (VI) with cyanogen bromide; and at a temperature in the range of from about 100° C. to about solvent reflux temperature, preferably at a temperature in the range of from about 120° C. to about 150° C., more preferably, at a temperature in the range of from about 125° C. to about 140° C., more preferably, at a temperature of about 135° C.; to yield a mixture comprising the corresponding compound of formula (I).

Preferably, the mixture comprising the compound of formula (I) is extracted with water; with the resulting biphasic mixture separated, the, bottom, aqueous layer (comprising inorganic salt impurities produced as by-product(s) of the reaction) discarded. One skilled in the art will recognize that the use of a low density secondary or tertiary alcohol as the solvent for the hydrolysis of the compound of formula (VII) with cyanogen bromide is additionally advantageous, as the water extraction to remove impurities (from the mixture comprising the desired compound of formula (I)) results in a biphasic mixture wherein the aqueous layer is the bottom layer, which bottom, aqueous layer can be easily separated and discarded (whereas the organic layer comprising the desired compound of formula (I) is the top layer and can be retained in the reactor).

The compound of formula (I) is preferably isolated from the organic layer according known methods, for example by evaporation of the solvent, selective precipitation, crystallization with a suitably selected anti-solvent (an anti-solvent such as heptane, cyclohexane, and the like, preferably heptane, and the like.

The compound of formula (I) is further, optionally purified according to known methods, for example by recrystallization from a suitably selected organic solvent such as a mixture of water and ethanol, and the like; to yield the compound of formula (I) as a solid, preferably as a crystalline solid.

The compound of formula (I) may be further reacted according to known methods, to yield buprenorphine or a pharmaceutically acceptable salt thereof, preferably the HCl salt thereof. In an example, the compound of formula (I) may be reacted with for example, (bromomethyl)cyclopropane, a known compound, according to known methods; and the resulting intermediate further reacted with a suitably selected demethylating agent, according to known methods; to yield buprenorphine. Alternatively, the compound of formula (I) is reacted with a suitably selected demethylating agent, according to known methods; and the resulting intermediate is then further reacted with for example, (bromomethyl)cyclopropane, a known compound, according to known methods; to yield buprenorphine. Buprenorphine may be further optionally reacted with a suitably selected acid, for example hydrochloric acid, according to known methods, to yield the corresponding acid addition salt (for example buprenorphine hydrochloride).

In one aspect, the process(es) of the invention have been unexpectedly found to advantageously decrease the amount of the undesired (β-isomer) in the final product. Although not intended to be definitive as to the mechanism, it is theorized that under the basic conditions of Grignard reaction, the alpha isomer (the compound of formula (III)) preferentially reacts with the Grignard reagent, and that the beta-isomer (the compound of formula (IV) may tautomerize to form the corresponding enol, and racemize before tautomerization back to the ketone. As a result, some of the undesired, β-isomer is converted into the desired a-isomer (and reacted with the Grignard reagent); effectively removing some of the undesired β-isomer from the product mixture and improving overall yield and/or purity of the desired product.

In another aspect, the process(es) of the invention have been unexpected found to advantageously allow for the telescoping (without isolation of one or more intermediate compound(s)) of two or more reaction steps in the synthesis of the compound of formula (I), buprenorphine or buprenorphine hydrochloride. In one aspect, the process(es) of the invention telescope (without isolation of intermediates) the three reaction steps which effect conversion of thebaine (preferably CPS thebaine) to the compound of formula (VI). In a second aspect, the process(es) of the invention telescope (without isolation of intermediates) the two reaction steps which effect conversion of the compound of formula (VI) to yield the compound of formula (I).

Pharmaceutical Compositions

In some embodiments, the invention further comprises pharmaceutical compositions containing a product prepared according to any of the processes described herein with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 1000 mg or any amount or range therein, and may be given at a dosage of from about 0.01 mg/kg/day to about 300 mg/kg/day, or any amount or range therein, preferably from about 0.01 mg/kg/day to about 50 mg/kg/day, or any amount or range therein, preferably from about 0.05 mg/kg/day to about 15 mg/kg/day, or any amount or range therein, preferably from about 0.05 mg/kg/day to about 5 mg/kg/day, or any amount or range therein. The dosages, however, may be varied depending upon the requirement of the patients, the severity of the condition being treated and the compound being employed. The use of either daily administration or post-periodic dosing may be employed.

Preferably the compositions of the invention are in unit dosage forms, such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 mg to about 1000 mg, or any amount or range therein, preferably from about 1 mg to about 500 mg, or any amount or range therein, preferably from about 2 mg to about 250 mg, or any amount or range therein, of the active ingredient of the invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol, and cellulose acetate The liquid forms in which the compositions of the invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone, or gelatin.

The method of treating disorders described in the invention may also be carried out using a pharmaceutical composition comprising any of the products as defined herein and a pharmaceutically acceptable carrier. The pharmaceutical composition may contain between about 0.5 mg and about 1000 mg of the compound, or any amount or range therein; preferably from about 1 mg to about 500 mg of the compound, or any amount or range therein, preferably from about 2 mg to about 250 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the invention may be administered in a single daily dose, or the total daily dosage may be administered in divided doses of two, three or four times daily. Furthermore, compounds for the invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methylcellulose and the like. For parenteral administration, sterile suspensions and solutions are desired. Isotonic preparations which generally contain suitable preservatives are employed when intravenous administration is desired.

To prepare a pharmaceutical composition of the invention, a product according to the invention, as the active ingredient, is intimately admixed with a pharmaceutical carrier according to conventional pharmaceutical compounding techniques, which carrier may take a wide variety of forms depending of the form of preparation desired for administration (e.g., oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets. Second Edition. Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of disorders described herein is required.

The daily dosage of the products may be varied over a wide range from about 0.01 mg to about 1,000 mg per adult human per day, or any amount or range therein. For oral administration, the compositions are preferably provided in the form of tablets containing about 0.01, 0.05, 0.1, 0.5, 1, 2.5, 4, 5, 10, 15, 25, 30, 40, 50, 60, 75, 80, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 500 mg/kg of body weight per day, or any amount or range therein. Preferably, the range is from about 0.05 to about 50 mg/kg of body weight per day, or any amount or range therein. More preferably, from about 0.05 to about 15 mg/kg of body weight per day, or any amount or range therein. More preferably, from about 0.05 to about 7.5 mg/kg of body weight per day, or any amount or range therein. More preferably, from about 0.05 to about 3 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

EXAMPLES

The following synthetic examples describe recipes/procedures for the synthesis of the title compounds. Several batches of the said compounds were prepared according to said recipes/procedures as described below.

Furthermore, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Synthesis Example 1: One Pot/Three Reaction Step Preparation of (S)-2-((4R,4aS,6R,7R,7aR,12bS)-7,9-dimethoxy-3-methyl-1,2,3,4,5,6,7,7a-octahydro-4a,7-ethano-4,12-methanobenzofuro[3,2-e]isoquinolin-6-yl)-3,3-dimethylbutan-2-ol

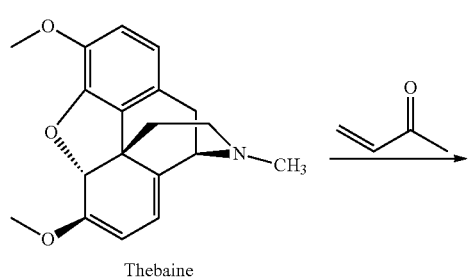

Thebaine

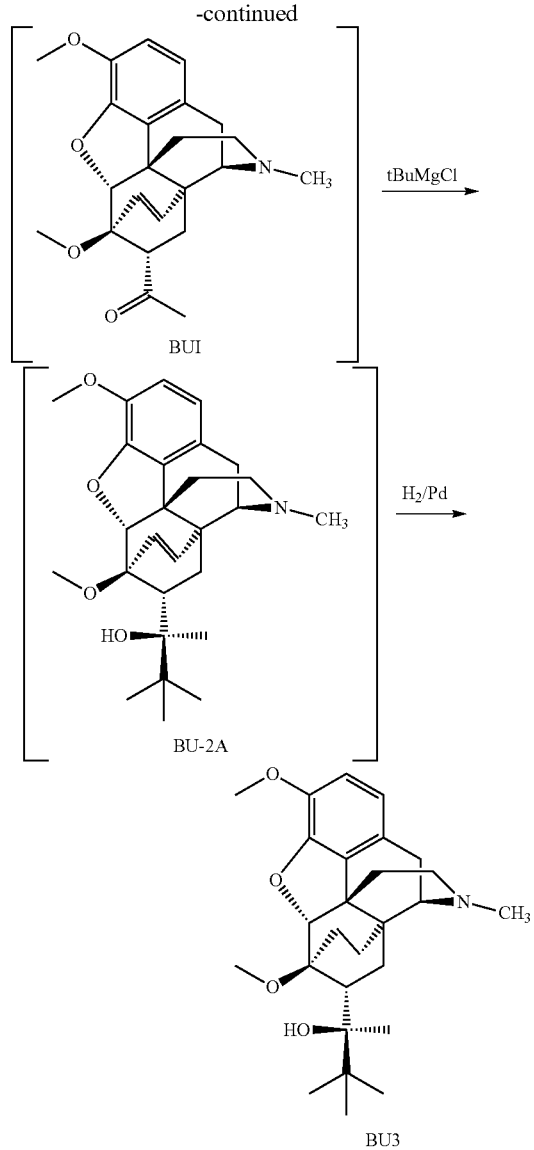

Step 1: Diels-Alder Reaction

To a 250 ml 3-necked jacketed round bottom flask (RBF) equipped with overhead agitation, condenser was charged CPS thebaine, (40 g) (46.94 g of actual wet thebaine, assay 85.9%), 2-propanol (96 ml), methylvinyl ketone (90%, 30 ml) and water (18.5 ml) (Total water=18.58 ml+ (46.56*14.1% Water)=25.14 ml). Without nitrogen purge, the resulting mixture was stirred at 245 rpm. The glycol water bath set to heat to 85° C. in 4 hours (reaction content temperature reached 80° C.) and the reaction mixture was held at a temperature of 80° C. for 12-20 hrs.

A representative sample of the reaction mixture prepared as described above was tested via HPLC with results as listed in Table 1, below.

TABLE 1

| Step 1 HPLC Results | | | | |
|---|---|---|---|---|
| Compound Name/ID | Retention Time | Area | % Area | Height |
| Thebaine (SM) | 6.647 | 5516 | 0.10 | 1109 |
| BU1 α-isomer | 9.472 | 5627529 | 97.59 | 1207614 |

TABLE 1-continued

Step 1 HPLC Results

| Compound Name/ID | Retention Time | Area | % Area | Height |
|---|---|---|---|---|
| BU1 β-isomer | 9.872 | 96885 | 1.68 | 21409 |
| Baseline peak (blank) | 13.541 | 9636 | 0.17 | 1613 |

A condenser was set up and a slight nitrogen purge was applied with a bath setting at 85° C. The reaction mixture was subjected to vacuum distillation until the reaction contents became viscous (The reaction content temperature dropped to 60.2° C. during the distillation). During distillation, toluene (130 ml, 1230 mmol, 100 mass %) was slowly added to continue the distillation. When the total collected distillate was ~60-70 ml, an additional portion of toluene (130 ml, 1230 mmol, 100 mass %) was added to the reaction mixture. When the total collected distillate was ~190 ml (The distillate was observed to be very cloudy; but became clear after settling for some time. Water (25 ml) was separated out from the cloudy mixture), a third portion of toluene (300 ml, 2840 mmol, 100 mass %) was added. The distillation was continued to the original volume of the reaction mixture (as measured prior to the solvent swap with toluene). (Note: Towards the end of distillation, the distillate looked very clear and homogeneous. The temperature during solvent swap never exceeded 70° C.).

The resulting anhydrous reaction mixture was cooled to 50° C. and then transferred to a pre-heated addition funnel. Fresh anhydrous toluene (20 ml) was used to rinse the reactor to the addition funnel. The reaction mixture was taken into the next step without further isolation of the intermediate BU1 product.

Step 2: Grignard Reaction

To a freshly dried 2-L 3-necked jacketed reactor, equipped with a distillation head, and a "Y" with an addition funnel and a thermocouple, was charged magnesium (29 g), THF (105 ml) and cyclohexane, and the resulting mixture agitated at 200 rpm (264 rpm towards the end of the addition when the slurry gets thicker). The mixture was then heated to reflux (water bath set at 83° C.), and 3-5% of the total solvent mass was distilled as a drying step (actual collected amount: ~30 ml). The temperature of the batch was adjusted to 64-66° C. (bath temperature at 68° C.). The temperature of the reaction mixture was then adjusted to 64-66° C. (Bath set at 68° C.). A 500 ml addition funnel was charged with 2-chloro-2-methylpropane (124 ml), cyclohexane and 5% of the above prepared t-butyl chloride solution (~12 ml), and the mixture added to the magnesium suspension. The resulting mixture was held with agitation until the Grignard formation reaction was initiated, as was determined by the internal batch temperature exceeding the jacket temperature by at least 2° C. (a thin, fine, gray-white slurry also begins to form once initiated). The remaining t-butyl chloride solution was then slowly added and the resulting exothermic reaction was allowed to slowly warm to reflux. Reflux began at about 70° C. and reached a maximum of about 74° C. at the end of the addition. Once addition of the t-butyl chloride solution was complete, the batch was held at 64-74° C. (Bath set at 68° C.) for 1 h and then cooled to 0° C. (water bath set at 0° C.) for a final reaction content temperature of ~5° C.

The anhydrous Diels-Alder reaction mixture in toluene after solvent swap (prepared as in Step 1 above) was then added over ~1 hr to the Grignard reagent (tert-butyl magnesium chloride prepared as described above), which had a temperature of 2° C. (water bath was set at 0° C.), at an agitation speed of ~338 rpm (Note: The temperature never exceeded 8° C. during the entire addition while with a bath temperature set at 0° C.). Fresh anhydrous toluene (20 ml) was used to rinse the addition funnel to the Grignard reaction (total 30 solution made up to (210 mL+20 mL rinse) and added to the reaction mixture. The water bath was set to 0° C. to hold the reaction mixture at about 2° c. The reaction mixture was held overnight (about 12 hours) at 2° C. then quenched with a cold (~4° C.) solution premade by mixing ammonium chloride (208 g) and water (867 g) in a 5 L three necked non-jacketed flask (Note: The transfer was exothermic and the quench vessel internal temperature was maintained at 0-30° C. (Record actual temperature: 25° C.)).

A representative sample of the reaction mixture prepared as described above was tested via HPLC with results as listed in Table 2, below.

TABLE 2

Step 2 HPLC Results

| Compound Name/ID | Retention Time | Area | % Area | Height |
|---|---|---|---|---|
| impurity (MW 383) | 7.829 | 222915 | 14.36 | 46606 |
| Starting Material | 9.424 | 54049 | 3.48 | 12057 |
| 17,18-DHBU3 β isomer | 14.550 | 5260 | 0.34 | 946 |
| 17,18-DHBU3 α isomer | 15.374 | 1259314 | 81.13 | 192629 |
| Cyclohexyl impurity | 17.949 | 10611 | 0.68 | 1438 |

Once the quench was complete, the mixture was held at 20-30° C. with 10 agitation for 30 min and then transferred to a separatory funnel. The lower aqueous layer was separated and discarded. (A small pad of CELITE was used to remove any rag layer, to facilitate phase separation). A buffer was prepared by combining water (663 ml), 85% phosphoric acid (63.7 g) and 28-30% ammonium hydroxide (29.7 g) and adjusting the pH to in the range of 3.8-4.0 (Actual: 3.93) with phosphoric acid and/or ammonium hydroxide. The organic layer was then washed twice with the buffer made above (Actual: 2×370 ml) followed by a single wash with water (100 ml).

The organic toluene/product layer (~750 ml) was treated with KBG CARBON (4 g) and diatomaceous earth at 65° C. for 1 hr; and the resulting mixture cooled to 45° C. The mixture was then filtered and the carbon cake washed with toluene (50 ml). The organic layer (700 g) was divided into 2 halves by weight (350 g×2). The first half was charged to a 1000 ml separation funnel. Water (100 ml) was added, followed by 50% $H_2SO_4$ (10.07 g) to pH 1.10 (at 28.2° C.); and the mixture shaken for 5 min to effect extraction. The biphasic mixture was allowed to settle, the bottom (aqueous) product layer was separated and retained. To the top (organic) layer was added fresh water (50 ml) for a second extraction. The mixture was shaken for 5 minutes to effect extraction. The biphasic mixture was allowed to settle, the bottom (aqueous) product layer was separated and retained. The top (organic) layer was discarded. The combined aqueous product layers were washed with a small amount of IPAc (25 ml) to remove any remaining traces of toluene in the aqueous layer (if any). The IPAc layer (~18 ml) was discarded. The aqueous layer was charged into 2 L jacketed reactor with a bottom valve. To the reactor was then added IPAc (150 ml), followed by 18% NaOH (~24 g) to adjust pH to 10.22, while maintaining the temperature at 25° C. The resulting mixture was heated to 65° C. to dissolve the solids. The resulting biphasic mixture was allowed to settle for separation. The bottom aqueous layer (250 ml) was collected into a 500-ml separatory funnel and extracted a second time with additional IPAc (50 ml). The bottom aqueous layer (250 ml) was discarded, while the top organic layers (containing the product) were combined for use in the next reaction step.

Step 3: Hydrogenation

The combined organic (IPAc) layers were divided into halves. One portion was charged into a 1-L hydrogenator (~15 ml IPAc was used as a rinse for the transfer) and subjected to hydrogenation with 20% Pd/C (2 g, Alfa Aesar 38308, Palladium, 20% on activated carbon powder, standard, reduced, nominally 50% water wet) at 60° C. (Bath set at 70° C.) and 65-70 psi (Regulator set at 60 psi), over about 2 days. The spent catalyst was filtered with a jacketed filter (Jacket temperature was set at 70° C.), and IPAc (137.82 g) was used to rinse the hydrogenator and catalyst wetcake. The filtrate was cooled to 50° C. and seeded with BU3 intermediate. The IPAc solvent was swapped with ethanol by distillation to a final content weight "Product+ethanol" of about 75 g. The resulting mixture was heated to reflux and held at reflux for 1 hour, then cooled to 5° C. The resulting precipitate was filtered and dried to a constant weight under a full vacuum at 45° C. Weight of product after drying=21.11 g (Yield: 75%).

A representative sample of the isolated solid product (BU3), prepared as described above, was tested by HPLC, with results as listed in the Table 3 below.

TABLE 3

Step 3 HPLC Results

| Compound Name/ID | Retention Time | Area | % Area | Height |
|---|---|---|---|---|
| BU3 β-isomer | 15.082 | 10414 | 0.17 | 1665 |
| BU3 α-isomer | 15.722 | 6262784 | 99.31 | 886680 |
| Desmethoxy impurity | 16.751 | 14408 | 0.23 | 2023 |
| Cyclohexanol impurity | 18.148 | 8451 | 0.13 | 1049 |

Synthesis Example 2: One Pot/Two Reaction Step Process in Preparation of (4R,4aS,6R,7R,7aR,12bS)-3-(cyclopropylmethyl)-6-((S)-2-hydroxy-3,3-dimethylbutan-2-yl)-7-methoxy-1,2,3,4,5,6,7,7a-octahydro-4a,7-ethano-4,12-methanobenzofuro[3,2-e]isoquinolin-9-ol

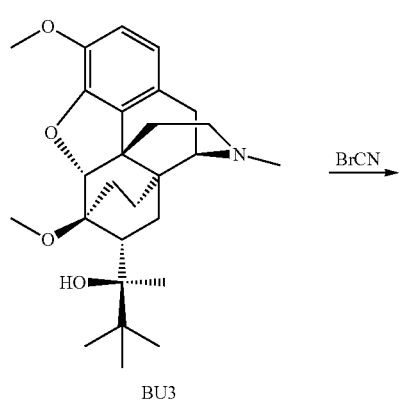

BU3

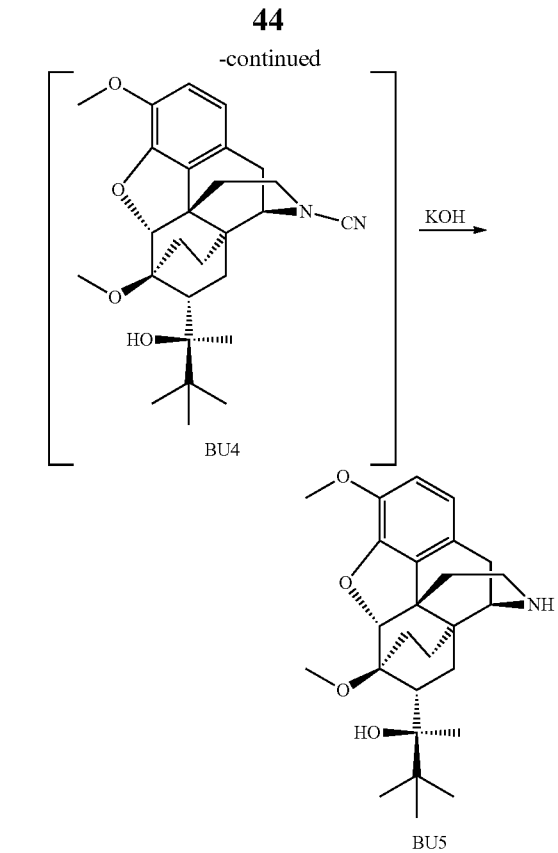

Step 1: Cyanogen Bromide Reaction

To a 250 ml reactor was charged BU3 (20 g), sodium carbonate (2 g) and cyclopentanol (80 ml). The reaction mixture was heated to 135° C. to remove trace amount of water in the reaction mixture, with a nitrogen purge (~25 ml of distillate was collected on the Dean-Stark apparatus). The reaction mixture was then cooled to 25° C. and cyanogen bromide (5M in acetonitrile, 20 ml) was added. The resulting mixture was heated to 40° C. and held at this temperature with stirring for 16 hours and 40 minutes.

A representative sample of the reaction mixture prepared as described above was tested via HPLC, with results as listed in Table 4, below.

TABLE 4

| Cyanogen Bromide Reaction | |
|---|---|
| Compound Name/ID | % Area |
| BU4 | 94.66 |
| Impurity 1 | 2.18% |
| Impurity 2 | 3.15% |
| BU3 | ND* |

*ND indicates that the compound was not detected

Step 2: Hydrolysis

The magnetic stirring bar in the reactor containing the reaction mixture prepared in Step 1 above was replaced with mechanical agitation. A distillation head was installed to the reactor and the resulting mixture was distilled at 60° C.-80° C. under vacuum to remove acetonitrile and excess/unreacted cyanogen bromide; to yield a cyclopentanol mixture containing the BU4 intermediate. The distillation head was swapped with a condenser. KOH pellets (12.6 g) were added to yield a light yellow to dark brown solution. Under nitrogen, the mixture was heated to 135° C. and held at 132° C.-136° C. for 3 hours.

The resulting mixture was cooled to 100° C. and water (50 ml) was added. The resulting mixture was stirred for 5 minutes and then allowed to settle, while maintaining the temperature at about 70° C. The resulting biphasic mixture was separated. The bottom aqueous layer was discarded. The top organic layer (containing the BU5 compound) was transferred to a clean reaction vessel and the cyclopentanol was distilled (to a net weight of 31.35 g). Heptane (106 ml) was added to the residue and the reaction mixture was heated to 95° C., resulting in a semi-clear solution. The solution was cooled to 0° C. The resulting solids were filtered off and washed with heptane (10 ml). The solids were dried to a constant weight (16.28 g, 84% yield. HPLC purity 96 area %) at 45° C. in an oven under a full vacuum; to yield the title compound (BU5).

While the foregoing specification teaches the principles of the invention, with examples provided for the purpose of illustration, it will be understood that the practice of the invention encompasses all of the usual variations, adaptations and/or modifications as come within the scope of the following claims and their equivalents.

A number of patent and non-patent publications may be cited herein in order to describe the state of the art to which this invention pertains. The entire disclosure of each of these publications is incorporated by reference herein.

While certain embodiments of the invention have been described and/or exemplified above, various other embodiments will be apparent to those skilled in the art from the foregoing disclosure. The invention is, therefore, not limited to the particular embodiments described and/or exemplified, but is capable of considerable variation and modification without departure from the scope and spirit of the appended claims.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All compounds, compositions, and processes described herein that embody the invention can, in alternate embodiments, be more specifically defined by any of the transitional terms "comprising," "consisting essentially of" and "consisting of."

What is claimed is:

1. A process for preparing (S)-2-((4R,4aS,6R,7R,7aR,12bS)-7,9-dimethoxy-1,2,3,4,5,6,7,7a-octahydro-4a,7-ethano-4,12-methanobenzofuro[3,2-e]isoquinolin-6-yl)-3,3-dimethylbutan-2-ol, comprising the steps of:

reacting a compound of formula (II) with methyl vinyl ketone, as illustrated in the following schematic:

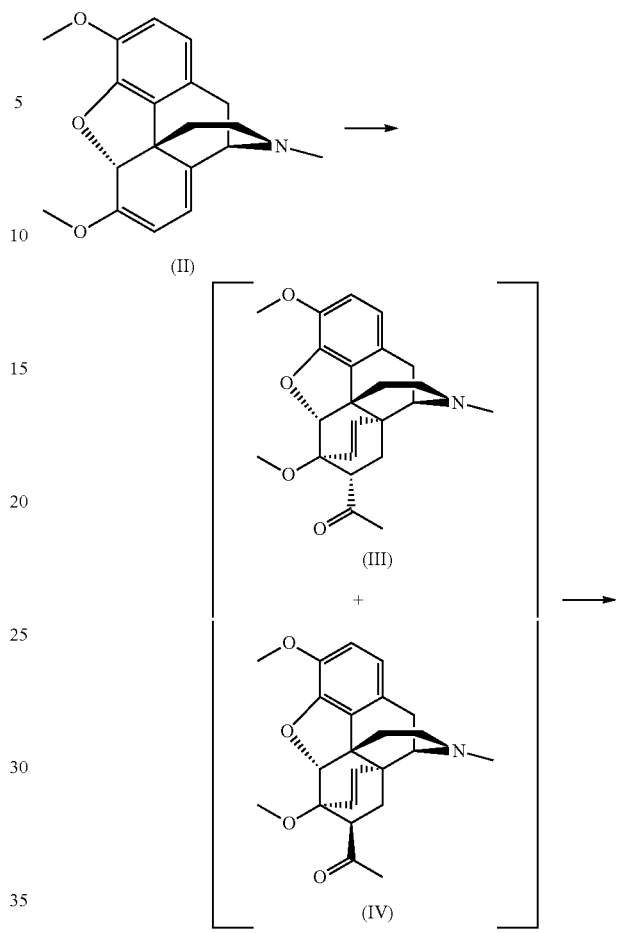

wherein the compound of formula (II) is combined with the methyl vinyl ketone in a solution that comprises an organic solvent, a mixture of organic solvents, or a mixture of water and an organic solvent, to provide a mixture of a compound of formula (III) and a compound of formula (IV);

azeotropically removing at least one of water and alcoholic solvent from the mixture of the compound of formula (III) and the compound of formula (IV) to provide an anhydrous mixture of the compound of formula (III) and the compound of formula (IV);

reacting the anhydrous mixture of the compound of formula (III) and the compound of formula (IV) with a Grignard reagent, as illustrated in the following schematic:

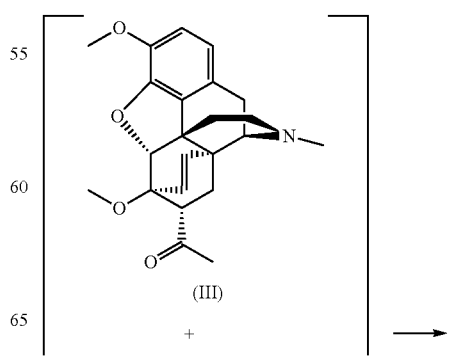

-continued

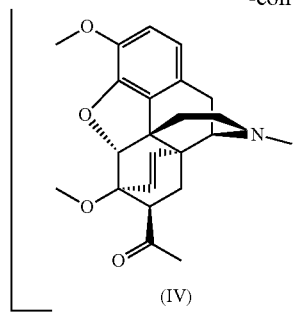

(IV)

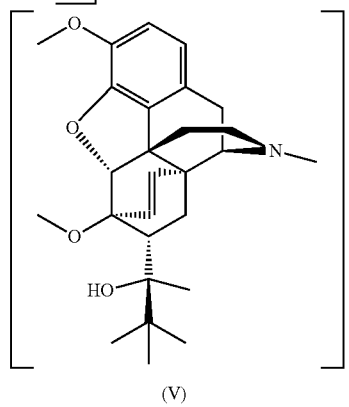

(V)

wherein the Grignard reagent is selected from the group consisting of t-butyl MgCl, t-butyl MgBr, and t-butyl MgI, to provide a mixture that comprises a compound of formula (V);

hydrogenating the compound of formula (V), as illustrated in the following schematic:

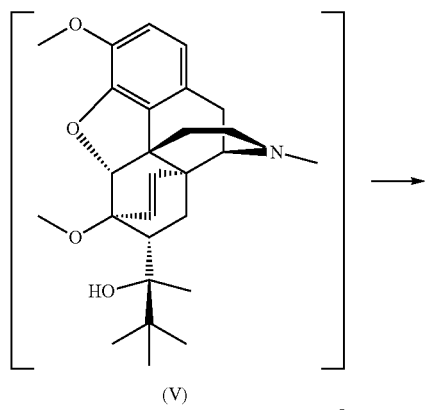

(V)

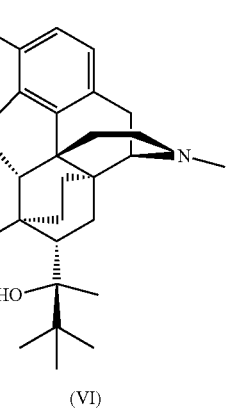

(VI)

to provide a mixture comprising a compound of formula (VI);

reacting the compound of formula (VI) with a source of cyanide in a first alcoholic solvent, as illustrated in the following schematic:

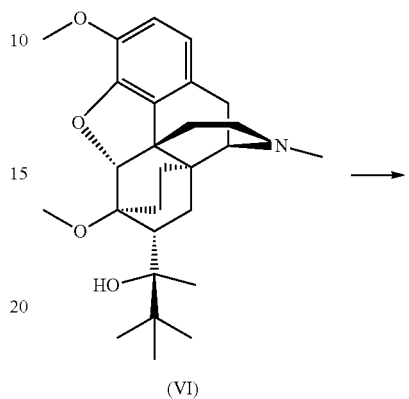

(VI)

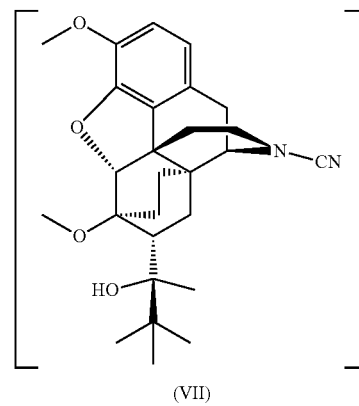

(VII)

wherein the first alcoholic solvent comprises one or more of a secondary alcohol and tertiary alcohol, and wherein the reaction optionally includes a first inorganic base, to provide a mixture that comprises a compound of formula (VII); and reacting the compound of formula (VII) with a second inorganic base in a second alcoholic solvent, as illustrated in the following schematic:

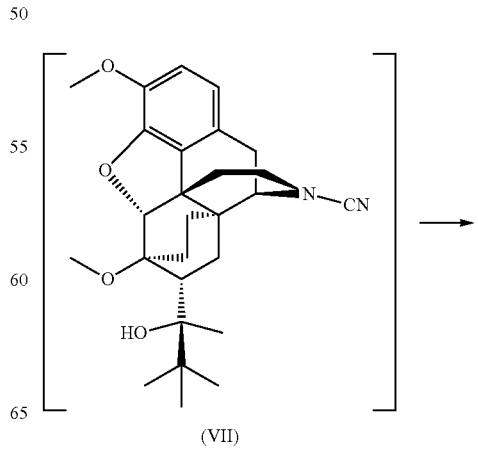

(VI)                    (VII)

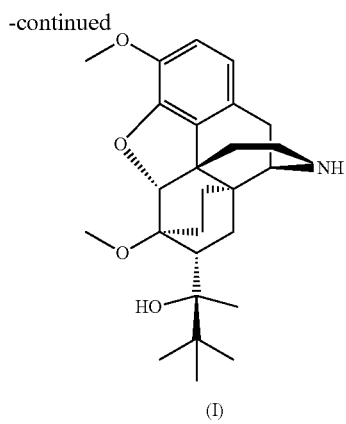

(I)

wherein the second alcoholic solvent includes one or more of a secondary alcohol and tertiary alcohol, to provide a mixture that comprises (S)-2-((4R,4aS,6R,7R,7aR,12bS)-7,9-dimethoxy-1,2,3,4,5,6,7,7a-octahydro-4a,7-ethano-4,12-methanobenzofuro[3,2-e]isoquinolin-6-yl)-3,3-dimethylbutan-2-ol (formula I).

2. The process of claim 1, wherein the step of reacting the compound of formula (II) comprises isolating the compound of formula (III) or the compound of formula (IV) from the mixture of the compound of formula (III) and the compound of formula (IV).

3. The process of claim 1, wherein the step of reacting the anhydrous mixture of the compound of formula (III) and the compound of formula (IV) comprises isolating the compound of formula (V) from the mixture that comprises a compound of formula (V).

4. The process of claim 1, wherein the step of hydrogenating the compound of formula (V) comprises isolating the compound of formula (VI) from the mixture that comprises the compound of formula (VI).

5. The process of claim 1, wherein the step of reacting the compound of formula (VI) comprises isolating the compound of formula (VII) from the mixture that comprises the compound of formula (VII).

6. The process of claim 1, wherein in the step of reacting the compound of formula (VI), the reaction comprises a first inorganic base.

7. The process of claim 6, wherein the first inorganic base is selected from the group consisting of sodium carbonate and potassium carbonate.

8. The process of claim 1, wherein the step of reacting the compound of formula (VII) comprises isolating (S)-2-((4R,4aS,6R,7R,7aR,12bS)-7,9-dimethoxy-1,2,3,4,5,6,7,7a-octahydro-4a,7-ethano-4,12-methanobenzofuro[3,2-e]isoquinolin-6-yl)-3,3-dimethylbutan-2-ol from the mixture that comprises (S)-2-((4R,4aS,6R,7R,7aR,12bS)-7,9-dimethoxy-1,2,3,4,5,6,7,7a-octahydro-4a,7-ethano-4,12-methanobenzofuro[3,2-e]isoquinolin-6-yl)-3,3-dimethylbutan-2-ol.

9. The process of claim 1, wherein the step of hydrogenating the compound of formula (V) comprises hydrogenating the compound of formula (V) with hydrogen gas in the presence of a Palladium catalyst.

10. The process of claim 1, wherein in the step of reacting the compound of formula (II), the solution comprises toluene, a mixture of toluene and water, or a mixture of isopropyl alcohol and water.

11. The process of claim 1, wherein the Grignard reagent is t-butyl MgCl.

12. The process of claim 1, wherein the source of cyanide comprises cyanogen bromide in acetonitrile or cyanogen bromide in dichloromethane.

13. The process of claim 1, wherein the first alcoholic solvent is selected from the group consisting of 2-pentanol, 4-methyl-2-pentanol, cyclopentanol, cyclohexanol, 3-ethyl-3-pentanol, and 2-methyl-2-hexanol.

14. The process of claim 1, wherein the second alcoholic solvent is selected from the group consisting of 2-pentanol, 4-methyl-2-pentanol, cyclopentanol, cyclohexanol, 3-ethyl-3-pentanol, and 2-methyl-2-hexanol.

15. The process of claim 1, wherein the first and second alcoholic solvent are the same.

16. The process of claim 1, wherein the first and second alcoholic solvent are selected from the group consisting of 4-methyl-2-pentanol and cyclopentanol.

17. The process of claim 1, wherein the second inorganic base is selected from the group consisting of potassium hydroxide and sodium hydroxide.

18. The process of claim 1, further comprising reacting (S)-2-((4R,4aS,6R,7R,7aR,12bS)-7,9-dimethoxy-1,2,3,4,5,6,7,7a-octahydro-4a,7-ethano-4,12-methanobenzofuro[3,2-e]isoquinolin-6-yl)-3,3-dimethylbutan-2-ol with at least one of a methylcyclopropane addition step and a demethylation step to prepare buprenorphine or a pharmaceutically acceptable salt thereof.

19. A process for preparing (S)-2-((4R,4aS,6R,7R,7aR,12bS)-7,9-dimethoxy-1,2,3,4,5,6,7,7a-octahydro-4a,7-ethano-4,12-methanobenzofuro[3,2-e]isoquinolin-6-yl)-3,3-dimethylbutan-2-ol or a pharmaceutically acceptable salt thereof, the process comprising the steps of:

reacting a compound of formula (VI) with a source of cyanide in a first alcoholic solvent, as illustrated in the following schematic:

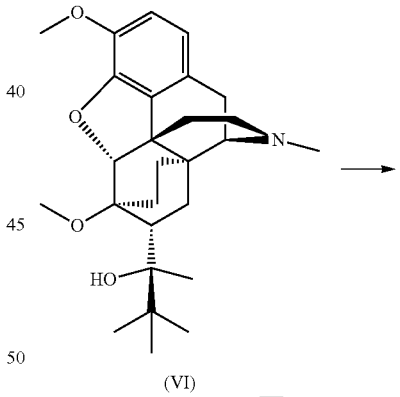

(VI)

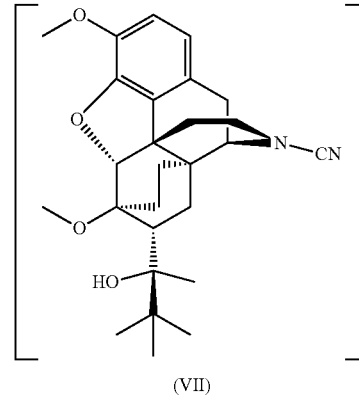

(VII)

wherein the first alcoholic solvent comprises one or more of a secondary alcohol and tertiary alcohol, and wherein the reaction optionally comprises a first inorganic base, to provide a mixture that comprises a compound of formula (VII), wherein the compound of formula (VII) is not isolated from the mixture that comprises the compound of formula (VII); and reacting the compound of formula (VII) with a second inorganic base in a second alcoholic solvent, as illustrated in the following schematic:

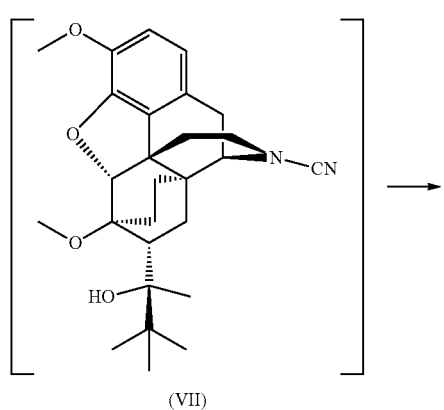

(VII)

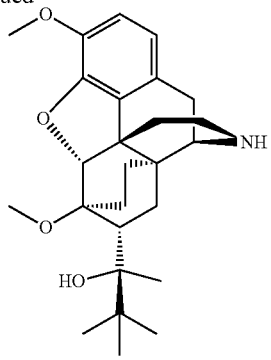

(I)

wherein the second alcoholic solvent comprises one or more of a secondary alcohol and tertiary alcohol, to provide a mixture that comprises (S)-2-((4R, 4aS,6R,7R,7aR,12bS)-7,9-dimethoxy-1,2,3,4,5,6,7,7a-octahydro-4a,7-ethano-4,12-methanobenzofuro[3,2-e]isoquinolin-6-yl)-3,3-dimethylbutan-2-ol (formula I);

wherein the process optionally comprises the step of isolating (S)-2-((4R,4aS,6R,7R,7aR,12bS)-7,9-dimethoxy-1,2,3,4,5,6,7,7a-octahydro-4a,7-ethano-4,12-methanobenzofuro[3,2-e]isoquinolin-6-yl)-3,3-dimethylbutan-2-ol from the mixture that comprises (S)-2-((4R,4aS,6R,7R,7aR,12bS)-7,9-dimethoxy-1,2,3,4,5,6,7,7a-octahydro-4a,7-ethano-4,12-methanobenzofuro[3,2-e]isoquinolin-6-yl)-3,3-dimethylbutan-2-ol.

* * * * *